(12) United States Patent
Iwanowicz et al.

(10) Patent No.: US 6,617,323 B2
(45) Date of Patent: Sep. 9, 2003

(54) AMINO-SUBSTITUTED COMPOUNDS USEFUL AS INHIBITORS OF IMPDH ENZYME

(75) Inventors: Edwin J. Iwanowicz, Cranbury, NJ (US); Katerina Leftheris, Skillman, NJ (US); Chunjian Liu, Lawrenceville, NJ (US); Toomas Mitt, Plainsboro, NJ (US); Scott H. Watterson, Hamilton, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 10/155,274

(22) Filed: May 23, 2002

(65) Prior Publication Data

US 2002/0183315 A1 Dec. 5, 2002

Related U.S. Application Data

(62) Division of application No. 09/428,609, filed on Oct. 27, 1999, now Pat. No. 6,420,403.
(60) Provisional application No. 60/106,184, filed on Oct. 29, 1998.

(51) Int. Cl.[7] .................... A61K 31/535; A61K 31/495; A61K 31/445; C07D 263/34; C07D 413/00
(52) U.S. Cl. .............................. 514/231.8; 514/254.02; 514/326; 514/340; 514/374; 544/138; 544/369; 546/208; 546/271.4; 548/236
(58) Field of Search .................. 548/236; 514/374, 514/231.8, 254.02, 326, 340; 544/138, 369; 546/208, 271.4

(56) References Cited

U.S. PATENT DOCUMENTS

| | | | |
|---|---|---|---|
| 4,686,234 A | 8/1987 | Nelson et al. | 514/469 |
| 4,725,622 A | 2/1988 | Nelson et al. | 514/469 |
| 4,727,069 A | 2/1988 | Nelson et al. | 514/211 |
| 4,763,935 A | 6/1988 | Allison et al. | 514/223.5 |
| 4,786,637 A | 11/1988 | Allison et al. | 514/233.5 |
| 4,808,592 A | 2/1989 | Nelson et al. | 514/233.5 |
| 4,861,776 A | 8/1989 | Nelson et al. | 514/233.5 |
| 4,868,153 A | 9/1989 | Allison et al. | 514/470 |
| 4,948,793 A | 8/1990 | Allison et al. | 514/233.5 |
| 4,952,579 A | 8/1990 | Nelson et al. | 514/233.5 |
| 4,959,387 A | 9/1990 | Nelson et al. | 524/469 |
| 4,992,467 A | 2/1991 | Allison et al. | 514/464 |
| 5,247,083 A | 9/1993 | Knox et al. | 544/153 |
| 5,380,879 A | 1/1995 | Sjogren | 514/464 |
| 5,444,072 A | 8/1995 | Patterson et al. | 544/153 |
| 5,665,583 A | 9/1997 | Collart et al. | 435/199 |
| 5,703,050 A | * 12/1997 | Klinger et al. | 514/18 |
| 5,773,646 A | * 6/1998 | Chandrakumar et al. | 562/439 |
| 5,807,876 A | 9/1998 | Armistead et al. | 514/374 |
| 6,054,472 A | 4/2000 | Armistead et al. | 514/374 |
| 6,255,323 B1 | * 7/2001 | Huang et al. | 514/313 |

FOREIGN PATENT DOCUMENTS

| | | |
|---|---|---|
| WO | WO94/01105 | 1/1994 |
| WO | WO94/12184 | 6/1994 |
| WO | WO97/40028 | 10/1997 |
| WO | WO98/40381 | 9/1998 |
| WO | WO99/55663 | 11/1999 |
| WO | WO00/56331 | 9/2000 |

OTHER PUBLICATIONS

Nature 256:331–333 (1975) Jackson et al.
J. Biol. Chem. 263:15769–15662 (1998) Collart et al.
J. Biol. Chem. 265: 5292 –5295 (1990) Natsumeda et al.
J. Biol. Chem. 266: 506–509 (1991) Weber.
J. Biol. Chem. 268: 27286–27290 (1993) Carr.

* cited by examiner

*Primary Examiner*—Bruck Kifle
(74) *Attorney, Agent, or Firm*—Laurelee A. Duncan

(57) ABSTRACT

The present invention discloses compounds useful in treating or preventing IMPDH-associated disorders, such as transplant rejection and autoimmune diseases, having the formula (I),

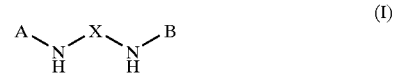

wherein X is —C(O)—, —C(S)—, or —S(O)$_2$—; A is an optionally-substituted saturated or unsaturated monocyclic or bicyclic ring; B is a saturated or unsaturated monocyclic or bicyclic ring system having at least one substituent Q which is selected from R$^7$ and R$^8$; R$^7$ is selected from (C$_0$–C$_6$)alkyl, (C$_2$–C$_6$)alkenyl and (C$_2$–C$_6$)alkynyl and R$^7$ is substituted with

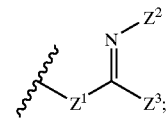

R$^8$ is selected from (C$_0$–C$_6$)alkyl, (C$_2$–C$_6$)alkenyl and (C$_2$–C$_6$)alkynyl and R$^8$ is substituted with

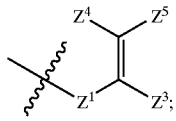

and Z$^1$ through Z$^5$ are as defined in the specification.

10 Claims, No Drawings

AMINO-SUBSTITUTED COMPOUNDS USEFUL AS INHIBITORS OF IMPDH ENZYME

RELATED INVENTIONS

This application is a divisional application of U.S. patent application Ser. No. 09/428,609, filed Oct. 27, 1999 now U.S. Pat. No. 6,420,403, which claims priority from provisional U.S. application Ser. No. 60/106,184, filed Oct. 29, 1998, which are incorporated herein by reference in their entirety.

FIELD OF THE INVENTION

The present invention relates to compounds that inhibit IMPDH. The invention also encompasses pharmaceutical compositions comprising these compounds and to methods for inhibiting the activity of IMPDH using the compounds of this invention and related compounds.

BACKGROUND OF THE INVENTION

Inosine monophosphate dehydrogenase (IMPDH) has been shown to be a key enzyme in the regulation of cell proliferation and differentiation. Nucleotides are required for cells to divide and replicate. In mammals, nucleotides may be synthesized through one of two pathways: the de novo synthesis pathway or the salvage pathway. The extent of utilization of each pathway is dependent on cell type. This selectivity has ramifications with regard to therapeutic utility as described below.

IMPDH is involved in the de novo synthesis of guanosine nucleotides. IMPDH catalyzes the irreversible NAD-dependent oxidation of inosine-5'-monophosphate ("IMP") to xanthosine-5'-monophosphate ("XMP"). Jackson et al., Nature, 256:331–333 (1975).

IMPDH is ubiquitous in eukaryotes, bacteria and protozoa. The prokaryotic forms share 30–40% sequence identity with the human enzyme.

Two distinct cDNA's encoding IMPDH have been identified and isolated. These transcripts are labeled type I and type II and are of identical size (514 amino acids). Collart et al., J. Biol. Chem., 263:15769–15772 (1988); Natsumeda et al., J. Biol. Chem., 265:5292–5295 (1990); and U.S. Pat. No. 5,665,583 to Collart et al. These isoforms share 84% sequence identity. IMPDH type I and type II form tetramers in solution, the enzymatically active unit.

B and T-lymphocytes depend on the de novo pathway, rather than the salvage pathway, to generate sufficient levels of nucleotides necessary to initiate a proliferative response to mitogen or antigen. Due to the B and T cell's unique reliance on the de novo pathway, IMPDH is an attractive target for selectively inhibiting the immune system without also inhibiting the proliferation of other cells.

Immunosuppression has been achieved by inhibiting a variety of enzymes. Examples include: phosphatase calcineurin (inhibited by cyclosporin and FK-506); dihydroorotate dehydrogenase (DHODase), an enzyme involved in the biosynthesis of pyrimidines (inhibited by leflunomide and brequinar); the kinase FRAP (inhibited by rapamycin); and the heat shock protein hsp70 (inhibited by deoxyspergualin).

Inhibitors of IMPDH have also been described in the art. WO 97/40028, U.S. Pat. Nos. 5,807,876, and 6,344,465 B1 describe a class of urea derivatives that possess a common urea backbone. A large number of compounds are described in WO 97/40028 and U.S. Pat. No. 5,807,876, but several of the compounds suffer from drawbacks such as inferior solubility. A recent publication, WO 98/40381, describes a series of heterocyclic substituted anilines as inhibitors of IMPDH.

U.S. Pat. Nos. 5,380,879 and 5,444,072 and PCT publications WO 94/01105 and WO 94/12184 describe mycophenolic acid ("MPA") and some of its derivatives as potent, uncompetitive, reversible inhibitors of human IMPDH type I and type II. MPA has been demonstrated to block the response of B and T-cells to mitogen or antigen. Immunosuppressants, such as MPA and derivatives of MPA, are useful drugs in the treatment of transplant rejection, autoimmune disorders, psoriasis, inflammatory diseases including rheumatoid arthritis, tumors, and allograft rejection. These are described in U.S. Pat. Nos. 4,686234, 4,725622, 4,727,069, 4,753,935, 4,786,637, 4,808,592, 4,861,776, 4,868,153, 4,948,793, 4,952,579, 4,959,387, 4,992,467, 5.247,083; and U.S. patent application Ser. No. 07/927,260, filed Aug. 7, 1992. However, MPA displays undesirable pharmacological properties, such as gastrointestinal toxicity and poor bioavailability.

Tiazofurin, ribavirin and mizoribine also inhibit IMPDH. Although these nucleoside analogs are competitive inhibitors of IMPDH, they also inhibit other NAD dependent enzymes. This low level of selectivity for IMPDH limits the therapeutic application of tiazofurin, ribavirin and mizoribine. Thus, new agents having improved selectivity for IMPDH would represent a significant improvement over the nucleoside analogs.

Mycophenolate mofetil, sold under the trade name CELLCEPT, is a prodrug which liberates MPA in vivo. It is approved for use in preventing acute renal allograft rejection following kidney transplantation. The side effect profile limits the therapeutic potential of this drug. MPA is rapidly metabolized to the inactive glucuronide in vivo. In humans, the blood levels of glucuronide exceed that of MPA. The glucuronide undergoes enterohepatic recycling causing accumulation of MPA in the bile and subsequently in the gastrointestinal tract. This together with the production of the inactive glucuronide effectively lowers the drug's in vivo potency, while increasing its undesirable gastrointestinal side effects.

Unlike type I, type II mRNA is preferentially upregulated in human leukemic cell lines K562 and HL-60. Weber, J. Biol. Chem., 266: 506–509 (1991). In addition, cells from human ovarian tumors and leukemic cells from patients with chronic granulocytic, lymphocytic and acute myeloid leukemias also display an up regulation type II mRNA. This disproportionate increase in IMPDH activity in malignant cells may be addressed through the use of an appropriate IMPDH inhibitor. IMPDH has also been shown to play a role in the proliferation of smooth muscle cells, indicating that inhibitors of IMPDH may be useful in preventing restenosis or other hyperproliferative vascular diseases.

IMPDH has been shown to play a role in viral replication in some viral cell lines. Carr, J. Biol. Chem., 268:27286–27290 (1993). The IMPDH inhibitor VX-497 is being evaluated for the treatment of hepatitis C virus in humans. Ribavirin has also been used in the treatment of hepatitis C and B viruses and when used in combination with interferon, an enhancement in activity was observed. The IMPDH inhibitor ribavirin is limited by its lack of a sustained response in monotherapy and broad cellular toxicity.

There remains a need for potent selective inhibitors of IMPDH with improved pharmacological properties, physical properties and fewer side effects. Such inhibitors would have therapeutic potential as immunosuppressants, anti-cancer agents, anti-vascular hyperproliferative agents, antu-inflammatory agents, antifungal agents, antipsoriatic agents, and anti-viral agents. The compounds of the present invention differ from those taught by the prior art and are effective inhibitors of IMPDH. All references cited herein are incorporated by reference in their entirety.

SUMMARY OF THE INVENTION

The present invention provides compounds of the following Formula I, and salts thereof, for use as inhibitors of IMPDH enzyme:

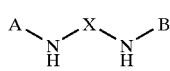
(I)

wherein:
X is selected from the group consisting of —C(O)—, —C(S)—, and —S(O)$_2$—;
A is a saturated or unsaturated monocyclic or bicyclic ring system optionally comprising up to 4 heteroatoms selected from N, O, or S, and wherein a CH$_2$ adjacent to any of said N, O, or S heteroatoms is optionally substituted with oxo (=O); and each ring is optionally substituted with up to 3 substituents, wherein:
  the first of said substituents, if present, is a group U, wherein U is selected from the group consisting of $R^1$, $R^2$, and $R^3$;
  the second of said substituents, if present, is selected from a group $U^1$, wherein $U^1$ is selected from the group consisting of $R^1$ and $R^2$; and
  the third of said substituents, if present, is selected from the group $U^1$;
$R^1$ is a saturated or unsaturated monocyclic ring having 4 to 6 members in the ring and wherein said ring optionally comprises up to 4 heteroatoms selected from N, O, and S, and wherein a CH$_2$ adjacent to any of said N, O, or S heteroatoms is optionally substituted with oxo (=O); and each $R^1$ optionally comprises up to 3 substituents selected from $R^2$ and $R^3$;
$R^2$ is selected from halogen, CN, NO$_2$, CF$_3$, —(C$_0$–C$_4$ alkyl)OR$^3$, OCF$_3$, OC(O)R$^3$, OC(O)OR$^3$, OC(O)NR$^3$R$^4$, —(C$_0$–C$_4$ alkyl) C(O)R$^3$, —(C$_0$–C$_4$alkyl)C(O)OR$^3$, —(C$_0$–C$_4$alkyl)C(O)NR$^3$R$^4$, —(C$_0$–C$_4$alkyl)CONR$^3$S(O)$_2$R$^5$, —(C$_0$–C$_4$alkyl)C(O)N(OR$^3$)R$^3$, —(C$_0$–C$_4$ alkyl)SR$^3$, —(C$_0$–C$_4$ alkyl)S(O)R$^5$, —(C$_0$–C$_4$alkyl)S(O)$_2$R$^5$, —(C$_0$–C$_4$ alkyl)NR$^3$S(O)$_2$R$^5$, —(C$_0$–C$_4$alkyl)S(O)$_2$OR$^3$, —(C$_0$–C$_4$ alkyl)P(O)(OH)OR$^3$, —J—(C$_1$–C$_4$ alkyl)OR$^3$, —J—(C$_1$–C$_4$ alkyl)C(O)OR$^3$, —J—(C$_1$–C$_4$ alkyl) CONR$^3$S(O)$_2$R$^5$, —J—(C$_1$–C$_4$ alkyl)S(O)$_2$NR$^3$R$^4$, —J—(C$_1$–C$_4$ alkyl)S(O)$_2$NR$^3$C(O) R$^4$, (C$_0$–C$_4$ alkyl)tetrazol-5-yl, and —J—(C$_1$–C$_4$ alkyl) tetrazol-5-yl, wherein J is chosen from O, S, and NR$^3$;
$R^3$ is selected from hydrogen, (C$_1$–C$_4$)alkyl, (C$_2$–C$_4$) alkenyl, (C$_2$–C$_4$)alkynyl, aryl(C$_0$–C$_4$)alkyl, heterocycle(C$_0$–C$_4$)alkyl, and cycloalkyl(C$_0$–C$_4$)alkyl, wherein said groups are substituted with 0–2 substituents independently selected from $R^6$;
$R^4$ is selected from hydrogen, (C$_1$–C$_4$)alkyl, (C$_2$–C$_4$) alkenyl, (C$_2$–C$_4$)alkynyl, aryl(C$_0$–C$_4$)alkyl, heterocycle(C$_0$–C$_4$)alkyl, cycloalkyl(C$_0$–C$_4$)alkyl, (C$_0$–C$_4$)alkylcarbonyl, aryl(C$_0$–C$_4$)alkylcarbonyl, heterocycle(C$_0$–C$_4$)alkylcarbonyl, (C$_1$–C$_4$) alkyloxycarbonyl, aryl(C$_1$–C$_4$)alkyloxycarbonyl, and heterocycle(C$_1$–C$_4$)alkyloxycarbonyl, wherein said groups are substituted with 0–2 substituents independently selected from $R^6$;
alternatively, $R^3$ and $R^4$, when both substituents are on the same nitrogen atom, as in (—NR$^3$R$^4$), can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups selected from the group consisting of oxo, $R^6$, (C$_1$–C$_6$)alkyl, C$_3$–C$_7$ cycloalkyl(C$_0$–C$_4$alkyl), (C$_1$–C$_6$)alkylcarbonyl, C$_3$–C$_7$cycloalkyl(C$_0$–C$_5$alkyl)carbonyl, C$_1$–C$_6$alkoxycarbonyl, C$_3$–C$_7$cycloalkyl(C$_0$–C$_5$ alkoxy)carbonyl, aryl(C$_0$–C$_5$alkyl), heterocycle(C$_0$–C$_5$ alkyl), aryl(C$_1$–C$_5$ alkoxy)carbonyl, heterocycle (C$_1$–C$_5$ alkoxy)carbonyl, (C$_1$–C$_6$)alkylsulfonyl, arylsulfonyl, and heterocyclesulfonyl,
wherein said aryl or heterocyclic groups are substituted with 0–2 substituents independently selected from the group consisting of C$_1$–C$_4$alkyl, C$_1$–C$_4$alkoxy, F, Cl, Br, CF$_3$, CN, and NO$_2$;
$R^5$ is selected from (C$_1$–C$_4$)alkyl, (C$_2$–C$_4$)alkenyl, (C$_2$–C$_4$)alkynyl, aryl(C$_0$–C$_4$) alkyl, heterocycle (C$_0$–C$_4$)alkyl, and cycloalkyl(C$_0$–C$_4$)alkyl, and each $R^5$ optionally comprises up to 2 substituents independently selected from $R^6$;
$R^6$ is selected from hydrogen, halogen, NO$_2$, CN, (C$_1$–C$_4$) alkyl, (C$_3$–C$_{10}$)cycloalkyl, (C$_2$–C$_6$)alkenyl, (C$_2$–C$_6$) alkynyl, haloalkyl, haloalkoxy, OH, hydroxy(C$_1$–C$_4$) alkyl, (C$_1$–C$_4$)alkoxy, (C$_1$–C$_4$alkyl)carbonyl, NH$_2$, (C$_1$–C$_4$alkyl)$_{1-2}$ alkylamino-, (C$_0$–C$_4$)alkylthio-, (C$_1$–C$_4$alkyl)sulfonyl-, aryl(C$_0$–C$_4$ alkyl)sulfonyl-, (C$_0$–C$_4$alkyl)$_{0-2}$aminosulfonyl-, (C$_0$–C$_4$ alkyl) carbonylaminosulfonyl-, aryl(C$_0$–C$_4$ alkyl) sulfonylaminocarbonyl, (C$_1$–C$_4$alkyl) sulfonylaminocarbonyl carboxylate, (C$_1$–C$_4$) alkyloxycarbonyl, (C$_0$–C$_4$alkyl)$_{0-2}$aminocarbonyl-, and (C$_0$–C$_4$ alkyl)tetrazol-5-yl;
B is a saturated or unsaturated monocyclic or bicyclic ring system optionally comprising up to 4 heteroatoms selected from N, O, and S, and wherein a CH$_2$ adjacent to any of said N, O, or S heteroatoms is optionally substituted with oxo (=O); wherein each B is substituted with one substituent Q which is selected from $R^7$ and $R^8$, and is optionally substituted with a second and/or a third substituent, wherein:
the second of said substituents, if present, is a group $U^2$, which is selected from $R^7$, $R^8$, $R^9$, $R^{10}$, $R^{11}$, and $R^{12}$; and
the third of said substituents, if present, is a group $U^3$, which is selected from $R^{10}$, $R^{11}$, and $R^{12}$;
$R^7$ is selected from (C$_0$–C$_6$)alkyl, (C$_2$–C$_6$)alkenyl and (C$_2$–C$_6$)alkynyl and $R^7$ is substituted with

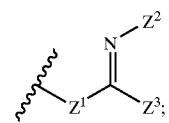

$R^8$ is selected from (C$_0$–C$_6$)alkyl, (C$_2$–C$_6$)alkenyl and (C$_2$–C$_6$)alkynyl and $R^8$ is substituted with:

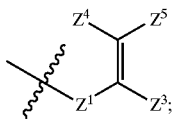

$R^9$ is selected from $(C_0-C_6)$alkyl, $(C_2-C_6)$alkenyl, and $(C_2-C_6)$alkynyl and $R^9$ is substituted with:

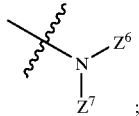

$Z^1$ is selected from O, S, and $NR^3$;
$Z^2$ is selected from hydrogen, $C_1-C_4$alkyl, $C_3-C_6$cycloalkyl, CN, $CF_3$, $OR^3$, heterocycle, $NO_2$, $C(O)R^3$, $C(O)_2R^3$, $C(O)NR^3R^4$, $S(O)_2NR^3R^4$, and $S(O)_2R^5$;
$Z^3$ is selected from $OR^3$, $SR^3$, and $NR^3R^4$;
$Z^4$ is selected from the group consisting of hydrogen, halogen, $C_1-C_4$ alkyl, $C_3-C_6$cycloalkyl, CN, $CF_3$, heterocycle, $NO_2$, $C(O)R^3$, $C(O)_2R^3$, $C(O)NR^3R^4$, $S(O)_2NR^3R^4$, and $S(O)_2R^5$;
$Z^5$ is selected from the group consisting of halogen, CN, $CF_3$, $NO_2$, $C(O)R^3$, $C(O)_2R^3$, $C(O)NR^3R^4$, $S(O)_2NR^3R^4$, and $S(O)_2R^5$;
$Z^6$ is selected from the group consisting of hydrogen, $C(O)R^3$, $C(O)OR^5$, $C(O)NR^3R^4$, $S(O)R^5$ and $S(O)_2R^5$;
$Z^7$ is selected from the group consisting of $OR^3$ and $NR^3R^4$,
$R^{10}$ is selected from hydrogen, $(C_1-C_4)$ alkyl, $(C_2-C_4)$ alkenyl, $(C_2-C_4)$alkynyl, aryl, heterocycle, and cycloalkyl, and each $R^{10}$ optionally comprises up to 3 substituents selected from $R^{11}$ and $R^{12}$;
$R^{11}$ is selected from hydrogen, halogen, $NO_2$, CN, $(C_1-C_4)$alkyl, $C_3-C_{10}$ cycloalkyl, $(C_2-C_6)$alkenyl, $(C_2-C_6)$alkynyl, haloalkyl, haloalkoxy, OH, $C_1-C_4$alkoxy, $C_1-C_4$alkylcarbonyl, $NH_2$, $(C_1-C_4$alkyl$)_{1-2}$alkylamino, $C_0-C_4$alkylthio, $C_1-C_4$ alkylsulfonyl, aryl$(C_0-C_4$alkyl$)$sulfonyl, $(C_0-C_4$alkyl$)_{0-2}$alkylaminosulfonyl-, $(C_0-C_4$ alkyl$)$carbonylaminosulfonyl-, aryl$(C_0-C_4$alkyl$)$sulfonylaminocarbonyl, $(C_1-C_4$alkyl$)$sulfonylaminocarbonyl carboxylate, $C_1-C_4$alkyloxycarbonyl, $(C_0-C_4$ alkyl$)_{0-2}$aminocarbonyl-, and $(C_0-C_4$alkyl$)$tetrazol-5-yl; and
$R^{12}$ is selected from hydrogen, alkyl, $(C_1-C_6)$alkoxy, $C_3-C_6$cycloalkyl, heterocycle and aryl.

Compounds of formula I, their enantiomers, diasteromers, tautomers and pharmaceutically acceptable salts, prodrugs and solvates thereof, are encompassed by the present invention and are novel.

The present invention also provides pharmaceutical compositions comprising the compounds of Formula I and methods of treating IMPDH-associated disorders using the compounds of Formula I.

The compounds of the present invention offer therapeutic advantages over known prior art compounds and are useful in treating IMPDH-associated disorders. These advantages include increased solubility (which in turn increases overall therapeutic benefit) and reduced negative side effects.

DETAILED DESCRIPTION OF THE INVENTION

In the description above and elsewhere in the specification, including the claims, each occurrence of a particular constituent is independent of each other occurrence of constituent(s), and independent of the character references associated with each constituent.

Listed below are definitions of various terms used in the specification and claims to describe the present invention.

The term "alkyl" refers to straight or branched chain alkyl.

The term "$C_{integer}-C_{integer}$" refers to a variable number of carbon atoms in a group depending on the integer values, as in $C_0-C_4$alkyl, which is meant to indicate a straight or branched alkyl group containing 0–4 carbon atoms. A group with 0 (zero) carbon atoms indicates that the carbon atom is absent i.e. there is a direct bond connecting adjacent terms. For example, the term "$C_0-C_4$alkylhydroxy" in the case "$C_0$" is meant to indicate the group hydroxy.

The term "halogen" or "halo" refers to fluorine, chlorine, bromine or iodine.

The term "aryl" refers to monocyclic or bicyclic aromatic hydrocarbons having 6 to 12 carbon atoms in the ring portion, such as phenyl, naphthyl, biphenyl and diphenyl groups which may be optionally substituted.

The term "alkenyl" refers to straight or branched chain alkenyl groups.

The term "alkynyl" refers to straight or branched chain alkynyl groups.

The term "cycloalkyl" refers to an optionally substituted, saturated cyclic hydrocarbon ring system.

When the term alkyl is used as a suffix following another group, as in arylalkyl, heterocycloalkyl or cycloalkylalkyl, this means the identified group is bonded directly through an alkyl group which may be branched or straight chain. For example, aryl$C_1$alkyl includes benzyl and naphtylmethyl. When the term alkyl is used as a prefix preceding another group, as in —$(C_0-C_4$ alkyl$)S(O)_2NR^3R^4$, —$(C_0-C_4$ alkyl$)S(O)_2NR^3C(O)R^4$, —$(C_0-C_4$ alkyl$)NR^3R^4$, $(C_1-C_4$alkyl$)_{1-2}$alkylamino-, $(C_1-C_4$alkyl$)$sulfonyl, and $(C_0-C_4$alkyl$)_{0-2}$aminocarbonyl, it is meant either that the identified group is bonded directly through an alkyl group which may be branched or straight chain or that the alkyl group (branched or straight chain) having the designated number of carbon atoms is attached by way of the specified group, which will be apparent to one skilled in the field, e.g., $(C_1-C_4$alkyl$)_{1-2}$alkylamino- includes groups such as —NH($CH_3$), —N($CH_3)_2$, NH(Et), —N($CH_3$)(Et), and so forth; $(C_0-C_4$alkyl$)_{0-2}$aminocarbonyl includes groups such as —C(=O)$NH_2$, —C(=O)NH($CH_3$), —C(=O)N($CH_3)_2$, —C(=O)NH(Et), —C(=O)N($CH_3$)(Et), and so forth; whereas —$(C_0-C_4$ alkyl$)NR^3R^4$ includes groups such as —$NR^3R^4$, —$CH_2NR^3R^4$, —$CH_2CH_2NR^3R^4$, and so forth.

The term "monocyclic" refer to either a "carbocyclic" or a "heterocyclic" ring system having one core ring which is optionally substituted, and "bicyclic" refers to carbocyclic or a heterocyclic ring systems having two core rings that are fused together, bridged, or joined together in a spiro fashion, which also is optionally substituted.

The term "carbocyclic" refer to an optionally substituted, fully saturated or unsaturated, aromatic or nonaromatic cyclic group, which is a 3 to 7 membered monocyclic, or a 7 to 11 membered bicyclic, and all the atoms in the ring are carbon atoms. Exemplary groups include phenyl, naphthyl, anthracenyl, cyclohexyl, cyclohexenyl, indanyl, bicyclo[2, 21]heptane, and the like.

When the term "unsaturated" is used herein to refer to a ring or group, the ring or group may be fully unsaturated or partially unsaturated.

Definitions for other groups that are recited are as follows: alkoxy is —OR, alkanoyl is —C(=O)R, aryloxy is —OAr, alkanoyloxy is —OC(=O)R, amino is —NH$_2$, alkylamino is —NHR, arylamino is —NHAr, aralkylamino is —NH—R—Ar, dialkylamino is —NRR, alkanoylamino is —NH—C(=O)R, alkylthio is —SR, alkylsulfonyl is —SO$_{(q)}$R, arylsulfonyl is —SO$_{(q)}$Ar, arylsulfonylamine is —NHSO$_{(q)}$Ar, alkylsulfonylamine is —NHSO$_2$R, sulfonamido is —SO$_2$NH$_2$, nitro is —NO$_2$, carboxy is —CO$_2$H, alkoxycarbonyl is —C(=O)OR, alkylcarbonyl is —C(=O)R, wherein R is alkyl or substituted alkyl, Ar is an aryl as defined above, and q is 2 or 3.

The terms "heterocycle" and "heterocyclic" refer to an optionally substituted, fully saturated or unsaturated, aromatic or nonaromatic cyclic group, which is a 3 to 7 membered monocyclic, or a 7 to 11 membered bicyclic, which have at least one heteroatom and at least one carbon atom in the ring. Each heterocyclic ring may contain 1, 2, 3, or 4 heteroatoms selected from nitrogen, oxygen and sulfur, where the nitrogen and sulfur heteroatoms may also optionally be oxidized and the nitrogen heteroatoms may also optionally be quaternized. The heterocyclic group may be attached via a nitrogen or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furanyl, tetrahydrofuranyl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane, tetrahydro-1,1-dioxothienyl, dioxanyl, isothiazolidinyl, thietanyl, thiiranyl, triazinyl, triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuranyl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), pyrrolo[1,2-a]pyridinyl, 1,3-dioxindanyl, dihydroisoindolyl, dihydroquinazolinyl (such as 3,4-dihydro-4-oxo-quinazolinyl), benzisothiazolyl, benzisoxazolyl, benzodiazinyl, benzothiopyranyl, benzotriazolyl, benzpyrazolyl, dihydrobenzofuranyl, dihydrobenzothienyl, dihydrobenzothiopyranyl, dihydrobenzothiopyranyl sulfone, dihydrobenzopyranyl, indolinyl, indolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

"IMPDH-associated disorders" refers to any disorder or disease state in which inhibition of the enzyme IMPDH (inosine monophosphate dehydrogenase, EC1.1.1.205, of which there are presently two known isozymes referred to as IMPDH type 1 and IMPDH type 2) would modulate the activity of cells (such as lymphocytes or other cells) and thereby ameliorate or reduce the symptoms or modify the underlying cause(s) of that disorder or disease. There may or may not be present in the disorder or disease an abnormality associated directly with the IMPDH enzyme.

Examples of IMPDH-associated disorders include transplant rejection and autoimmune disorders, such as rheumatoid arthritis, multiple sclerosis, juvenile diabetes, asthma, and inflammatory bowel disease, as well as inflammatory disorders, cancer and tumor disorders, T-cell mediated hypersensitivity diseases, ischemic or reperfusion injury, viral replication diseases, proliferative disorders and vascular diseases.

As used herein the term "treating" includes prophylactic and therapeutic uses, and refers to the alleviation of symptoms of a particular disorder in a patient, the improvement of an ascertainable measurement associated with a particular disorder, or the prevention of a particular immune response (such as transplant rejection). The term "patient" refers to a mammal, preferably a human.

The compounds of this invention may contain one or more asymmetric carbon atoms and thus may occur as racemates and racemic mixtures, single enantiomers, diastereomeric mixtures and individual diastereomers. All such isomers of the compounds disclosed herein are expressly included within the scope of the present invention. Each stereogenic carbon may be of the R or S configuration.

Some of the compounds described herein contain olefinic double bonds, and unless specified otherwise, are meant to include both E and Z geometric isomers. For example, fragment AA also implies fragment AB as shown below.

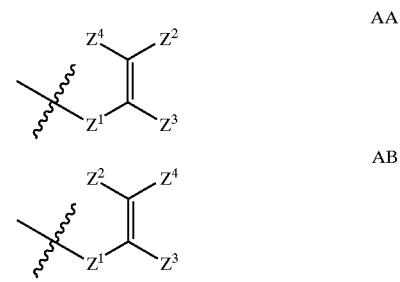

Combinations of substituents and variables thereof that result in stable compounds are also contemplated within the present invention. The term "stable" as used herein refers to compounds which possess stability sufficient to allow for their manufacture and which maintain their integrity for a sufficient period of time to be useful as therapeutic or diagnostic agents.

As used herein, the compounds of this invention are defined to include pharmaceutically acceptable derivatives and prodrugs thereof. A "pharmaceutically acceptable derivative or prodrug" includes any pharmaceutically acceptable salt, ester, salt of an ester, or other derivative of a compound of the present invention which, upon administration to a subject, is capable of providing (directly or indirectly) a compound of the invention. Particularly favored derivatives and prodrugs are those that increase the bioavailability of the compounds of the present invention when such compound is administered to a subject (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to a compound of the present invention.

Pharmaceutically acceptable salts of the compounds disclosed herein include those derived from pharmaceutically acceptable inorganic and organic acids and bases known to those skilled in the art. Examples of suitable acid salts include, but are not limited to, the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, trifluoroacetic, tosylate and undecanoate. Other acids, for example oxalic, while not in themselves pharmaceutically acceptable, may be employed in the preparation of salts useful as intermediates in obtaining the compounds of the present invention and their pharmaceutically acceptable acid additional salts.

Salts derived from appropriate bases include, but are not limited to, the following: alkali metal (e.g., sodium), alkaline earth metal (e.g., magnesium), ammonium and N—$(C_{1-4}$ alkyl$)_4^+$ salts. The present invention also envisions the quaternization of any basic nitrogen-containing groups of the compounds disclosed herein. Water- or oil-soluble or dispersible products may be obtained by such quaternization.

Preferred Compounds

Preferred are compounds of the Formula I represented by the following Formula IA, including stereoisomeric forms thereof, tautomeric forms thereof, pharmaceutically acceptable salt forms thereof, or prodrug forms thereof:

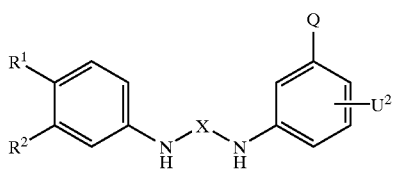

(IA)

wherein $U^2$ is $R^{10}$ or $R^{11}$;

$Z^2$ is selected from the group consisting of CN, $CF_3$, $OR^3$, heterocycle, $C(O)R^3$, $C(O)_2R^3$, $C(O)NR^3R^4$, $S(O)_2NR^3R^4$, and $S(O)_2R^5$; and $Z^4$ is selected from the group consisting of halo, CN, $CF_3$, $NO_2$, $C(O)R^3$, $C(O)_2R^3$, $C(O)NR^3R^4$, $S(O)_2NR^3R^4$, and $S(O)_2R^5$;

and all other constituents are as previously described for compounds of Formula I.

Methods of Production

The compounds of the present invention may be synthesized using conventional techniques known in the art. Advantageously, these compounds are conveniently synthesized from readily available starting materials. Following are general synthetic schemes for manufacturing compounds of the present invention. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to give the desired compound(s).

The preparation of cyanoguanidines useful to this invention are described in Scheme 1a. An aniline or heterocyclic amine can react with a variety of isocyanates which are either commercially available or readily prepared by several methods such as reaction of an amine with phosgene and a base such as triethylamine, or reaction with triphosgene, to form a urea such as 1a.1. Amines may be prepared by many methods such as displacement of a halide by potassium pthalimide, and liberation of the amine by the action of hydrazine, or reduction of a nitro group or a nitrile. Nitriles may be reduced to amines (such as 1a.2) by many methods including those detailed in Hudlicky, M., "Reductions in Organic Chemistry", 2nd Ed., ACS Monograph 188, (1996), at pp. 239–245 (American Chemical Society, Washington, D.C.) Cyanoguanidines are conveniently prepared by reaction with the commercially available reagent diphenyl cyanocarbonimidate to initially provide an intermidiate imidate such as 1a.3, which is then reacted with an amine either neat or in a solvent at elevated temperatures in a sealed reaction vessel to provide a cyanoguanidine such as 1a.4

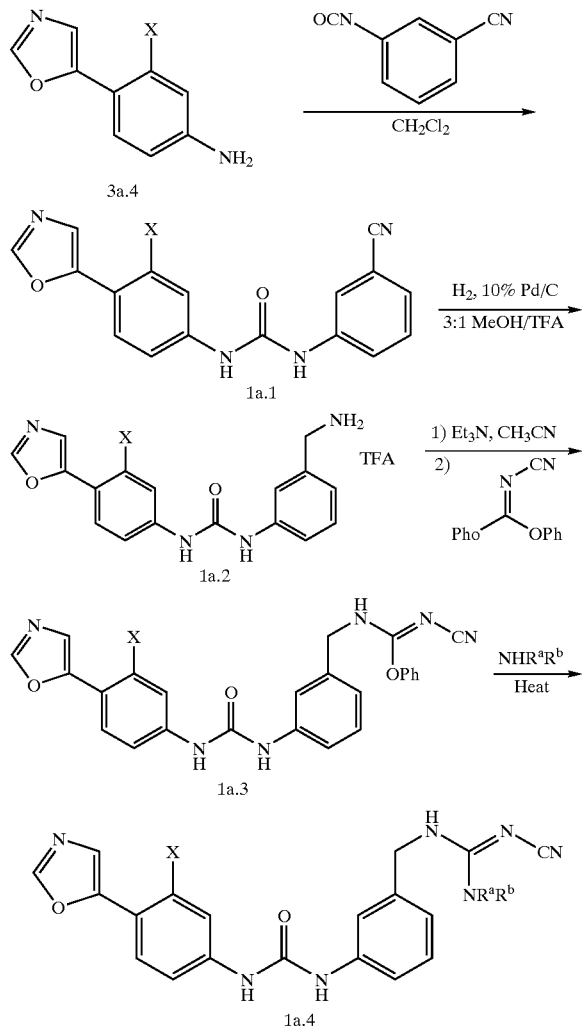

Cyanoimidates useful to this invention are also conveniently prepared from the intermediate cyanoimidate 1a.3 by reaction with an alcohol in the presence of either sodium metal, or a hydride base such as sodium hydride to provide 1b.1.

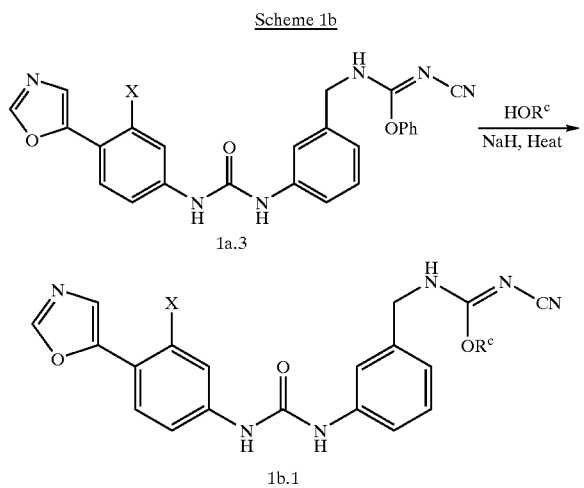

HOR$^C$ = an alcohol

Alkenes useful to this invention may be prepared by several methods including that depicted in scheme 1c. The preparation of nitroalkenes from amines has been describe in many references including Schulze et al., *Arch Pharm* (1994) 327 (7), at pp. 455–462, and from sulfonamides by Masereel et al., *Eur J. Med. Chem* (1997) 32(5), at pp. 453–456. In this case, the reaction of an amine such as 1a.2, with the commercially available reagent 1,1-bis(methylthio)-2-nitroethylene provides the thioalkene 1c.1. This may also be a useful intermediate, since it can further react with an amine to provide the bis-aminoalkene 1c.2. Alternatively, thioalkene 1c.1 can react with a sulfonamide in the presence of base to provide bis-aminoalkene 1c.3.

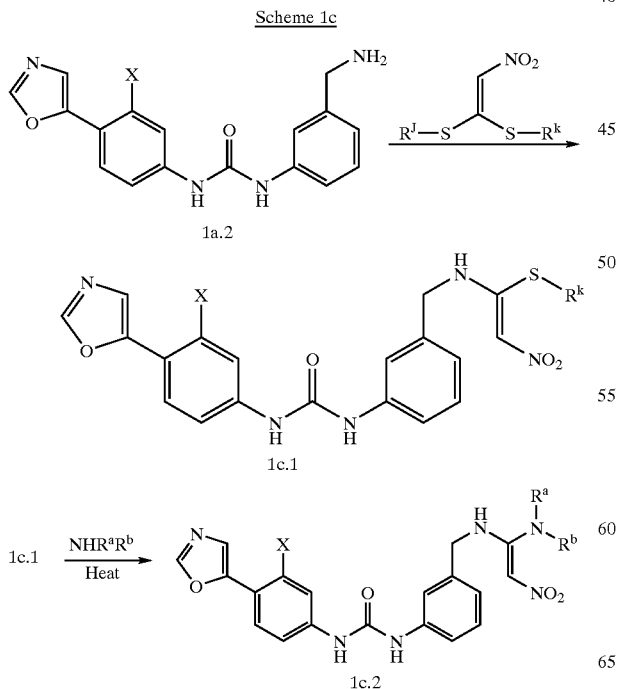

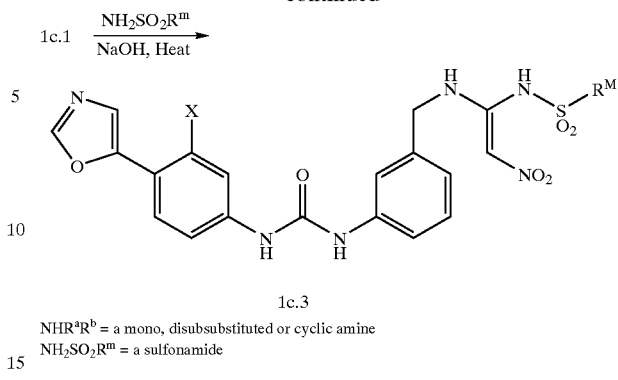

NHR$^a$R$^b$ = a mono, disubstituted or cyclic amine
NH$_2$SO$_2$R$^m$ = a sulfonamide Cyanoguanidines of type 2a.2 are also useful to this invention and may be prepared from an aniline such as 3, or heterocyclic amine by reaction with diphenyl cyanocarbonimidate in a manner similar to that described for scheme 1a, to provide 2a.1. In this case, the intermediate imidate 2a.1 is reacted with an monosubstituted amine to provide compound 2a.2.

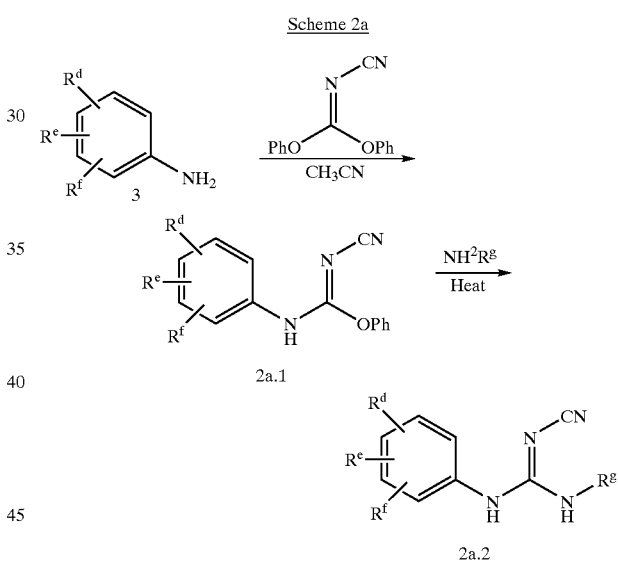

NH$_2$R$^g$ = a monosubstituted amine

Alkenes of type 2b.2 are also useful to this invention, and may be prepared from an aniline such as 3, or heterocyclic amine by reaction with 1,1-bis(methylthio)-2-nitroethylene in a similar manner to that described for scheme 1b to provide 2b.1. In this case, the intermediate thioalkene 2b.1 is reacted with a monosubstituted amine to provide alkene 2b.2

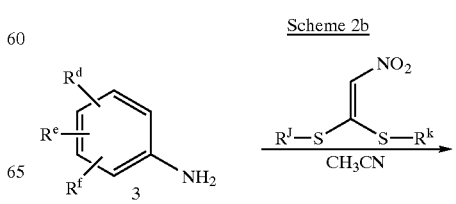

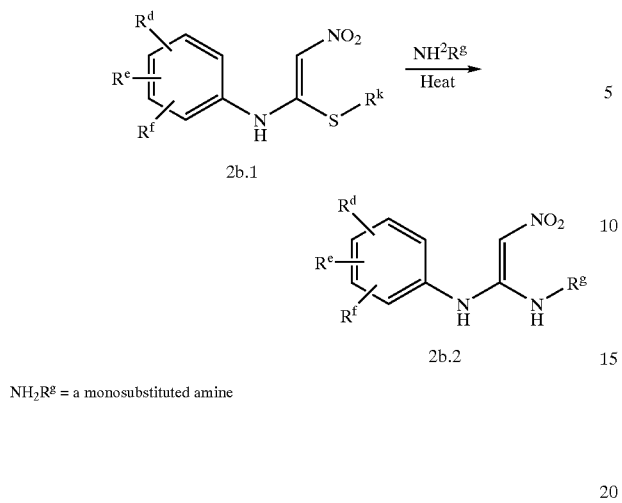

NH₂Rᵍ = a monosubstituted amine

Alkenes useful to this invention may also be prepared as described in scheme 2c, by the reaction of a carbon nucleophile with a carbodiimide. Carbodiimides may be prepared by several methods including desulfurization of a thiourea with reagents such as methanesulfonyl chloride in the presence a base and catalytic N,N-dimethylaminopyridine (DMAP), or by the use of 1,1'thiocarbonyldi-2,2'-pyridone and catalytic DMAP as described by Kim S., and Yi, K.Y., in *J. Org. Chem.* 1986, 51, 2613–2615. Thioureas are readily prepared by several methods including reaction of a urea with Lawesson's reagent, or by reaction of an amine with an isothiocyanate. Isothiocyanates are either commercially available or readily prepared by reaction of an amine with 1,1'thiocarbonyldi-2,2'-pyridone. In this case, an aniline or heterocyclic amine such as 3, may be reacted with the commercially available reagent 1,1'thiocarbonyldi-2, 2'pyridone (2c.1) to provide isothiocyante 2c.2. Reaction of the isothiocyante with a monosubstituted amine provides thiourea 2c.3. The thiourea is converted to the carbodiimide by reaction with 1,1'thiocarbonyldi-2,2'pyridone (2c.1) in the presence of a catalytic amount of DMAP to provide 2c.4. The intermediate carbodiimide may react with a variety of activated carbon nucleophiles in the presence of a suitable base capable of preparing the corresponding anion of the carbon nucleophile of interest. For example, a variety of substitued alkenes of type 2c.6 where the electron withdrawing group (EWG) is a nitro group may be prepared by reaction of a nitroalkane (2c.5, EWG=NO₂) which is either commercially available, or readily prepared by one skilled in the art of organic synthesis, with carbodiimide 2c.4, in the presence of a base (for example, see Moimas et al.; Synthesis [1985], at 509). Sulfones (2c.5, EWG=SO₂R) or nitrites (2c.5, EWG=CN) may also be used as activated carbon nucleophiles of type 2c.5 in the presence of a suitable base to provide alkenes of type 2c.6. Alternatively activated carbon nucleophiles with two electron withdrawing groups of type 2c.7 are also useful to this invention and are either commercially available or can be readily prepared by one skilled in the art of organic chemistry. Reaction of carbodiimide 2c.4 with active methylene compounds of type 2c.7 in the presence of a base provide alkenes of type 2c.7 (for example, see Stephen, A., *Montsh Chem* (1966), at p. 97).

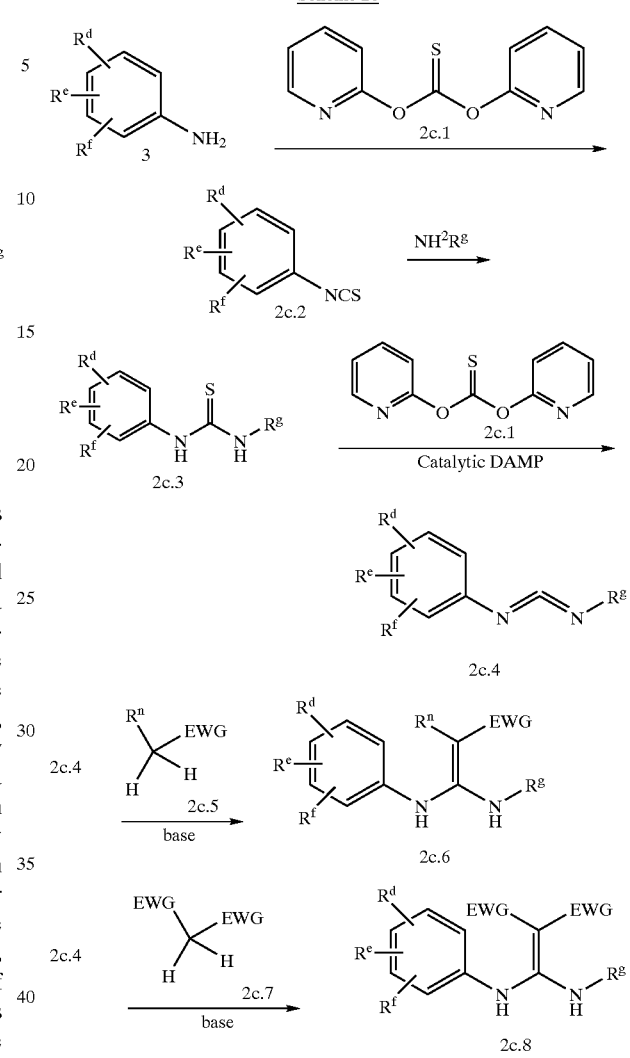

NH₂Rᵍ = a monosubstituted amine
EWG = electron withdrawing group such as CO₂R, NO₂, SO₂R, CN, etc.

Cyanoguanidines may also be prepared from thiouronium salts as illustrated in scheme 2d. An isothiocyanate (such as 2c.2) is reacted with sodium cyanamide, which is prepared by reaction of sodium metal with cyanamide in a solvent such as MeOH or EtOH, to produce thiouronium salt 2d.1. Addition of an amine in the presence of a coupling agent such as 1-(3-dimethylaminopropyl)-3-ethylcarbodiimide hydrochloride (EDC) provides the desired cyanoguanidine 2a.2

Scheme 2d

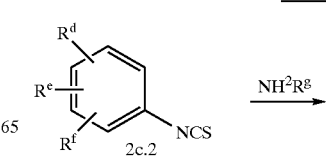

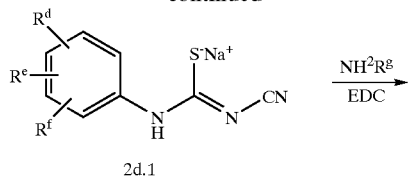

2d.1

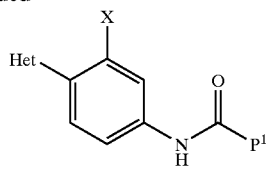

3a.2

R = H, Alkyl
X = H, OMe, etc.
HET = a 5 or 6 membered ring containing at least one O, N, S atom with an unsaturated bond directly attached to the bromine
P¹ = alkyl, O-benzyl, O-tertbutyl, ect.

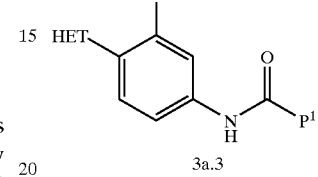

2a.2

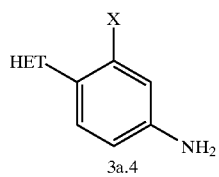

3a.3

Amines of type 3a.4 useful to prepare compounds of this invention may be commercially available or can be readily prepared by many methods known to one skilled in the art of organic chemistry. See, e.g., Richard C. Larock, *Comprehensive Organic Transformations. A Guide to Functional Group Preparation*, pp. 385–439 (VCH Publishers, Inc. 1989). Examples include, but are not limited to, reduction of a nitro group, reduction of an azide and reduction of a nitrile and are detailed in schemes 3a to 3d.

A general method for the synthesis of an amine useful in this invention can be perfomed by metal-catalyzed cross-coupling methods known in the literature. The simplest case is a Suzuki type cross-coupling (Miyaura et al., *Synth. Comm.* 11(7):513–519 (1981); Suzuki et al., *J. Am. Chem. Soc.* 111:513 (1989); and Kalinin, *Russ. Chem. Rev.* 60:173 (1991)) of an aryl boronic acid or ester (3a. 1) (as shown below) with an appropriate bromoheterocycle in the presence of a suitable catalyst such as tetrakis(triphenylphosphine) palladium. After the cross coupling has been performed, the product may be deprotected. The choice of protecting group and its method of removal will be readily apparent to one skilled in the art of organic chemistry. Such considerations and methods are, for example, described by Greene and Wuts, *Protective Groups in Organic Synthesis* (2d Ed., John Wiley and Sons, Inc., New York, N.Y. [1991]). For example, if the protecting group is acetyl, the product may be deprotected by treatment with aqueous potassium hydroxide at a concentration of 0.5N to 5 N at rt to 100° C. for a period between 0.5 h and 24 h.

For example aryl boronic acid (3a.5) may react with the known 5-bromothiazole (3a.6) in the presence of tetrakis(triphenylphosphine) palladium (0), to provide (3a.7) which may be deprotected by an appropriate method.

Scheme 3a

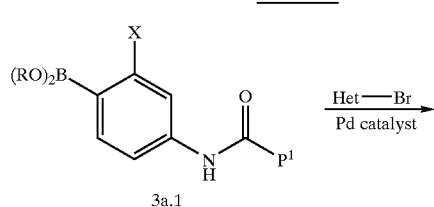

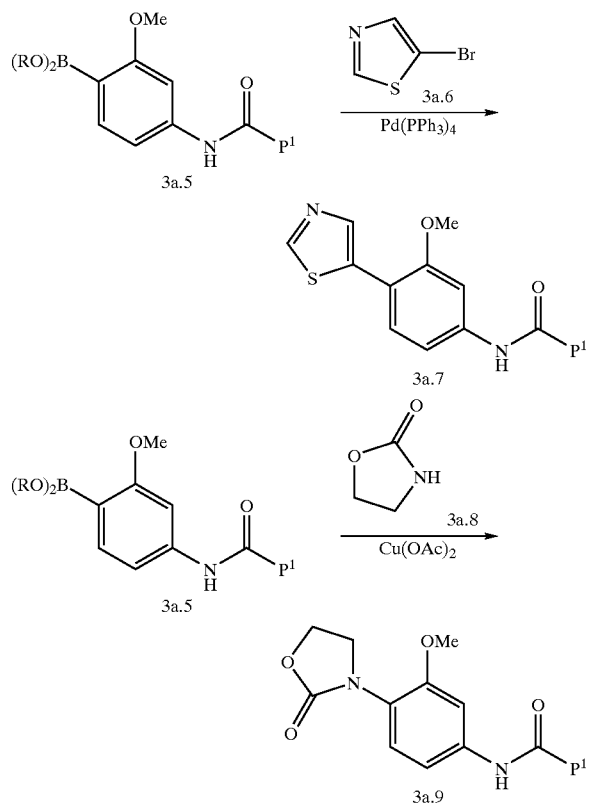

Copper is an effective catalyst for cross coupling of aryl boronic acids to N-unsubstituted heterocycles as described by Chan. et al., *Tetrahed. Lett.* 39:2933–2936 (1998); and Lam et al., *Tetrahed. Lett.* 39:2941–2944 (1998). This results in compounds in which the heterocycle is attached to the aryl ring through nitrogen rather than carbon. For example, aryl boronic acid (3a.5) may react with oxazolone (3a.8) in the presence of copper (II) acetate in the presence of an amine base such as pyridine to provide intermediate (3a.9) which may be deprotected by an appropriate method In general, aryl boronic acids and esters, 3b.3, where X is not Br or I, may be prepared as shown in Scheme 3b, from the corresponding arylbromide (3b. 1) by treatment with a palladium catalyst such as [1,1'-Bis(diphenylphosphino)-ferrocene] dichloropalladium (II) and bis(pinacolato) diboron, (3b.2), as reported by Ishayama et al., *J. Org. Chem.,* (1995) 7508–7510. Aryl boronic esters may be converted to the corresponding boronic acid by several methods including treatment with aqueous HCl. In a variation of the synthesis, the nitrogen may be masked as a nitro group and later reduced by several means including metal reductions, such as by treatment with tin chloride in HCl or by refluxing the nitro compound with zinc in the presence of $CaCl_2$ in a solvent such as EtOH, or in certain cases the nitro group may be reduced by catalytic hydrogenation in the presence of catalysts such as palladium on carbon. The conditions for the reduction of nitro groups are detailed in several references including Hudlicky, M., "Reductions in Organic Chemistry", 2nd Ed., ACS Monograph 188, 1996, pp 91–101 American Chemical Society, Washington, D.C. A second variation of the synthesis allows the aryl bromide to remain through the entire synthesis and elaborated to the boronic acid at the end. This may eliminate the need for a protecting group.

Scheme 3b

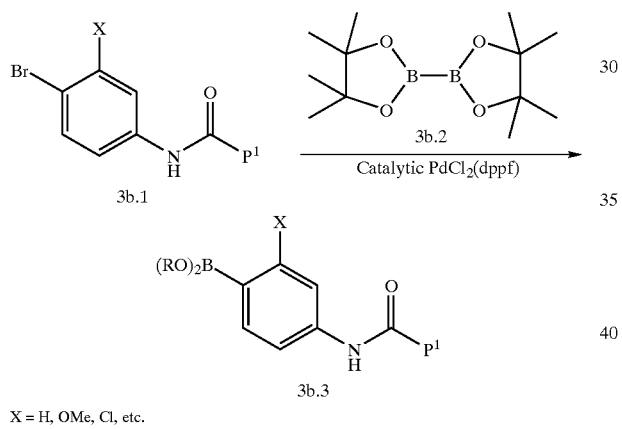

X = H, OMe, Cl, etc.
P1 = alkyl, Obenzyl, Otertbutyl, etc.

In certain cases, it may be more expedient to construct the heterocyclic ring by other methods. A general method for the synthesis of 5-membered heterocycles includes the 1,3-dipolar cycloaddition reaction, which is well known to one skilled in the art of organic chemistry and is described by Padwa, Albert (Editor) in "1,3-Dipolar Cycloaddition Chemistry, Vol. 2" (John Wiley and Sons, New York, N.Y. [1984]); and Padwa, Albert (Editor) in "1,3-Dipolar Cycloaddition Chemistry, Vol. 1" (John Wiley and Sons, New York, N.Y. [1984]). For example, oxazoles may be prepared by 1,3 dipolar cycloaddition of the corresponding aldehyde (3c.1) and (p-tolylsulfonyl)methyl isocyanate (TOSMIC) (3c.2) as shown in scheme 3c. The aldehyde may be commercially available or prepared from the corresponding methyl group by oxidation with reagents such as $CrO_3$, $MnO_2$, and ammonium cerium (IV) nitrate by methods well known to one skilled in the art of organic chemistry and described in Hudlicky, M., "Oxidations in Organic Chemistry", ACS Monograph 186 (1990), American Chemical Society, Washington, D.C. The nitro group in intermediate (3c.3), is reduced to an amine (3c.4), as discussed above.

Scheme 3c

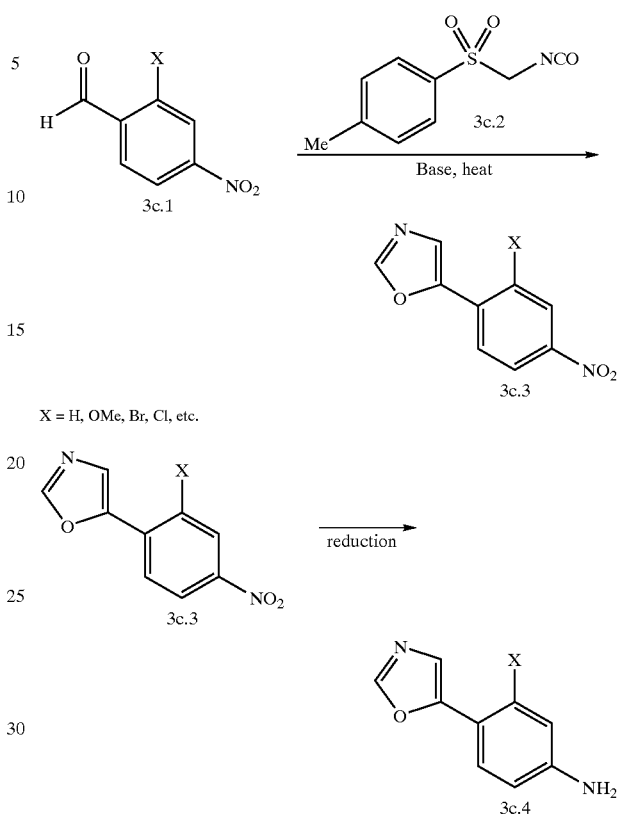

X = H, OMe, Br, Cl, etc.

An alternative method of producing amines useful to this invention is by nucleophilic attack of an electron deficient ring system as outlined in scheme 3d. Halonitrobenzenes (3d. 1), are either commercially available or can be readily prepared by methods known to one skilled in the art of organic synthesis. Displacement with a variety of nucleophiles produces compounds of structure (3d.2). In one example, heating (3d.3) with a nucleophilic heterocycle such as triazole with or without the addition of a base provides the intermediate nitro compound which may be reduced as previously described to provide aimnes (3d.4). Alternatively, simple organic nucleophiles such as cyamide can be reacted with halonitrobenzene (3d.5) to provide an intermediate nitrocompound which can be reduced to amine (3d.6).

Scheme 3d

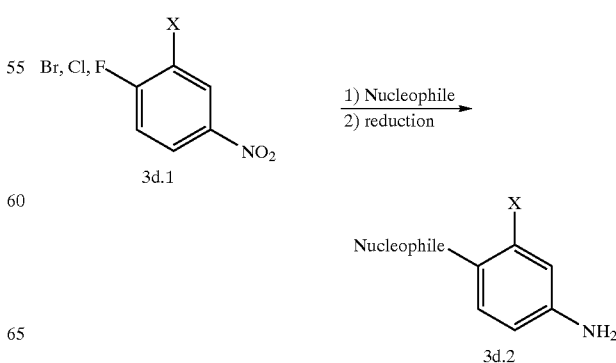

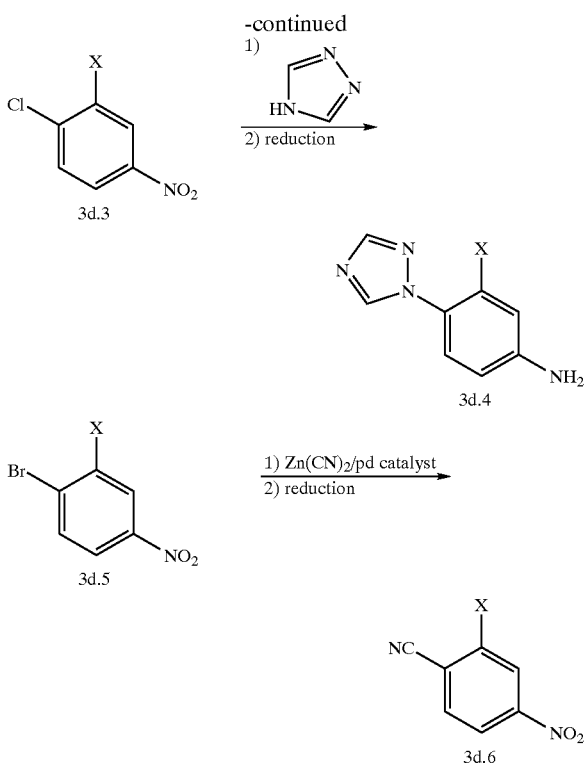

The compounds of the present invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Utility

The compounds of the present invention inhibit IMPDH enzyme and are thus useful in the treatment, including prevention and therapy, of disorders which are mediated or effected by cells which are sensitive to IMPDH inhibition. The present invention thus provides methods for the treatment of IMPDH-associated disorders, comprising the step of administering to a subject in need thereof at least one compound of Formula I in an amount effective therefor. Other therapeutic agents, such as those described below, may be employed with the inventive compounds in the present methods. In the methods of the present invention, such other therapeutic agent(s) may be administered prior to, simultaneously with, or following the administration of the compound(s) of the present invention.

Use of the compounds of the present invention in treating IMPDH-associated conditions is exemplified by, but is not limited to, treating a range of disorders such as: treatment of transplant rejection, such as kidney, liver, heart, lung, pancreas (e.g., islet cells), bone marrow, cornea, small bowel, skin allografts, skin homografts (such as employed in burn treatment), heart valve xenografts, serum sickness, and graft vs. host disease; in the treatment of autoimmune diseases, such as rheumatoid arthritis, psoriatic arthritis, multiple sclerosis, juvenile diabetes, asthma, inflammatory bowel disease (such as Crohn's disease and ulcerative colitus), pyoderma gangrenum, lupus (systemic lupus erythematosis), myasthenia gravis, psoriasis, dermatitis, dermatomyositis, eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoinimune hypopituatarism, Guillain-Barre syndrome, and alveolitis; in the treatment of T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); in the treatment of inflammatory diseases such as osteoarthritis, acute pancreatitis, chronic pancreatitis, asthma, acute respiratory distress syndrome, Sezary's syndrome and vascular diseases which have an inflammatory and or a proliferatory component such as restenosis, stenosis and artherosclerosis; in the treatment of cancer and tumor disorders, such as solid tumors, lymphomas and leukemia; in the treatment of fungal infections such as mycosis fungoides; in protection from ischemic or reperfusion injury such as ischemic or reperfusion injury that may have been incurred during organ transplantation, myocardial infarction, stroke or other causes; in the treatment of DNA or RNA viral replication diseases, such herpes simplex type 1 (HSV-1), herpes simplex type 2 (HSV-2), hepatitis (including hepatitis B and hepatitis C) cytomegalovirus, Epstein-Barr, and human immunodeficiency virus (HIV).

Additionally, IMPDH is also known to be present in bacteria and thus may regulate bacterial growth. As such, the IMPDH-inhibitor compounds of the present invention may be useful in treatment or prevention of bacterial infection, alone or in combination with other antibiotic agents.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

The present invention also provides pharmaceutical compositions comprising at least one of the compounds of Formula I, or a pharmaceutically-acceptable salt thereof, capable of treating an IMPDH-associated disorder in an amount effective therefor, alone or in combination with at least one additional therapeutic agent, and any pharmaceutically acceptable carrier, adjuvant or vehicle. "Additional therapeutic agents" encompasses, but is not limited to, an agent or agents selected from the group consisting of an immunosuppressant, an anti-cancer agent, an anti-viral agent, an anti-inflammatory agent, an anti-fungal agent, an antibiotic, or an anti-vascular hyperproliferation compound.

The term "pharmaceutically acceptable carrier, adjuvant or vehicle" refers to a carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-3-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the Formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to IMPDH-associated disorders.

The compounds of the present invention may be employed alone or in combination with each other and/or other suitable therapeutic agents useful in the treatment of IMPDH-associated disorders, such as IMPDH inhibitors other than those of the present invention, immunosuppressants, anti-cancer agents, anti-viral agents, anti-inflammatory agents, anti-fungal agents, antibiotics, or anti-vascular hyperproliferation agents.

Exemplary such other therapeutic agents include the following: cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins constructed from CD40 and/or CD154/gp39 (e.g., CD40Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, celecoxib and rofecoxib, steroids such as prednisone or dexamethasone, gold compounds, antiviral agents such as abacavir, antiproliferative agents such as methotrexate, leflunomide, FK506 (tacrolimus, Prograf), cytotoxic drugs such as azathiaprine and cyclophosphamide, TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art.

Compounds disclosed herein are capable of targeting and inhibiting IMPDH enzyme. Inhibition can be measured by various methods, including, for example, IMP dehydrogenase HPLC assays (measuring enzymatic production of XMP and NADH from IMP and NAD) and IMP dehydrogenase spectrophotometric assays (measuring enzymatic production of NADH from NAD). See, e.g., Montero et al., *Clinica Chimica Acta* 238:169–178 (1995). Additional assays known in the art can be used in ascertaining the degree of activity of a compound ("test compound") as an IMPDH inhibitor. The inventors used the following assay to determine the degree of activity of the compounds disclosed herein as IMPDH inhibitors:

Activity of IMPDH I and IMPDH HI was measured following an adaptation of the method described in WO 97/40028. The reaction mixture was prepared containing 0.1M Tris pH 8.0, 0.1 M KCl, 3 mM EDTA, 2 mM DTT, 0.4 mM IMP and 40 nM enzyme (IMPDH I or IMPDH II). The reaction was started by the addition of NAD to a final concentration of 0.4 mM. The enzymatic reaction was followed by measuring the increase in absorbance at 340 nM that results from the formation of NADH. For the analysis of potential inhibitors of the enzyme, compounds were dissolved in DMSO to a final concentration of 10 mM and added to the assay mixture such that the final concentration of DMSO was 2.5%. The assay was carried out in a 96-well plate format, with a final reaction volume of 200 R1.

Compounds disclosed herein are capable of inhibiting the enzyme IMPDH at a measurable level, under the above-described assay or an assay which can determine an effect of inhibition of the enzyme IMPDH.

The following examples illustrate preferred embodiments of the present invention and do not limit the scope of the present invention which is defined in the claims. Abbreviations employed in the Examples are defined below.

| Abbreviations | |
|---|---|
| Ac | Acetyl |
| AcOH | Acetic acid |
| aq. | Aqueous |
| CDI | Carbonyldiimidazole |
| Bn | Benzyl |
| Boc | tert-butoxycarbonyl |
| DCM | Dichloromethane |
| DMAP | Dimethylaminopyridine |
| DMSO | Dimethylsulfoxide |
| EDC | 1-(3-Dimethylaminopropyl)-3-ethylcarbodiimide hydrochloride |
| EtOAc | Ethyl acetate |

| Abbreviations | |
|---|---|
| Et | Ethyl |
| EtOH | Ethanol |
| h | Hours |
| i | iso |
| HPLC | High pressure liquid chromatography |
| HOAc | Acetic acid |
| THF | Tetrahydrofuran |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| M$^+$ | (M + H)$^+$ |
| M$^{+1}$ | (M + H)$^+$ |
| MS | Mass spectrometry |
| n | normal |
| Pd/C | Palladium on carbon |
| Ph | Phenyl |
| Pr | Propyl |
| Ret Time | Retention time |
| rt or RT | Room temperature |
| sat'd | Saturated |
| TFA | Trifluoroacetic acid |
| THF | Tetrahydrofuran |
| TOSMIC | Tosylmethyl isocyanide |
| YMC | YMC mc, Wilmington, NC 28403 |

EXAMPLE 1

Preparation of N-[3-[[[(Cyanoamino)phenoxymethylene]amino]methyl]phenyl]-N'-[3-methoxy-4-(5-oxazolyl)phenyl]urea

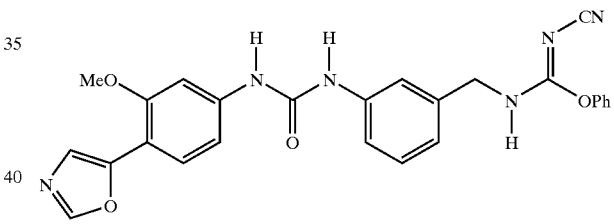

1A. Preparation of 4-Nitro-2-methoxy-(a,a-bisacetoxy)toluene

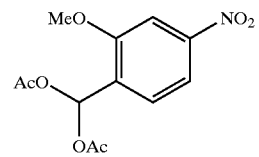

To a 5 L three necked round bottom flask equipped with a mechanical stirrer was added 4-nitro-2-methoxytoluene (150.0 g, 0.8973 mol), HOAc (900 mL) and Ac$_2$O (900 mL). The mixture was stirred and cooled to 8° C. with an acetone/ice bath. Concentrated H$_2$SO$_4$ (136 mL) was carefully added while keeping the pot temperature <190 C. After cooling to 0° C., CrO$_3$ (252.6 g, 2.526 mol, 2.815 equiv.) was added portion-wise over 1 hour while maintaining the reaction temperature between 0–10° C. After the addition, the mixture was stirred at 0° C. for 30 minutes at which time the reaction was complete. The reaction mixture was then carefully poured into ice (1.5 kg) with stirring to give a slurry. The remaining black gummy residue was rinsed with HOAc (3×100 mL), and the washes were added to the slurry. After stirring for 10 minutes, the slurry was filtered. The cake was washed with water (3×400 mL) and suction dried for 17 hours to give 4-nitro-2-methoxy-(a,a-bisacetoxy) toluene (1A, 129.0 g, 51%). $^1$H NMR (CDCl$_3$) d 8.02 (s, 1H), 7.89 (d, J=8.4 Hz, 1H), 7.77 (s, 1H), (d, 8.4 Hz, 1H), 3.98 (s, 3H), 2.16 (s, 6H).

1B. Preparation of 4-Nitro-2-methoxybenzaldehyde

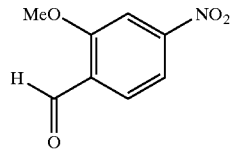

To a 2 L rounded bottom flask equipped with a condenser and a mechanical stirrer was placed 1A (250.7 g, 0.8851 mol), dioxane (300 nL) and concentrated HCl (60 mL). The reaction mixture was heated to reflux and stirred under N$_2$ for 20 hours. Water (250 mL) was added dropwise while maintaining the reaction mixture at reflux. After cooling to 0° C. with an ice/water bath, the resulting slurry was stirred for 30 minutes and then filtered. The cake was washed with water (4×200 mL) and suction dried for 17 hours to give 4-nitro-2-methoxybenzaldehyde (1B, 146.3 g, 91%) as yellow solid. $^1$H NMR (CDCl$_3$) d 10.54 (s, 1H), 8.00 (d, J=8.3 Hz, 1H), 7.91 (s, 1H), 7.89 (d, J=8.3 Hz, 1H), 4.08 (s, 3H).

1C. Preparation of 5-(4-Nitro-2-methoxyphenyl)oxazole

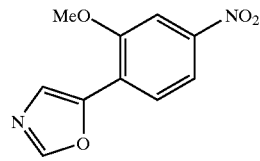

To a 5 L three necked round bottom flask equipped with a condenser and a mechanical stirrer was placed 1B (146.3 g, 0.8076 mol), TOSMIC (157.7 g, 0.8077 mol), K$_2$CO$_3$ (116.6 g, 0.8075 mol) and MeOH (2.5 L). The mixture was heated to reflux under N$_2$ and stirred for 3 hours. Water (1.25 L) was added drop-wise while maintaining the pot temperature between 59-69° C. The resulting slurry was cooled to room temperature, and then to 5° C. with an ice-water bath. After stirring for 30 minutes at 5° C., the slurry was filtered. The resulting cake was washed with water (3×400 mL) and dried in a vacuum oven at 45° C. for 20 hours to give 5-(4-nitro-2-methoxyphenyl)oxazole (IC, 148.5 g, 84%) as a yellow-reddish solid. $^1$H NMR (CDCl$_3$) d 8.02 (s, 1H), 7.97 (d, J=2 Hz, 1H), 7.95 (d, J=2 Hz, 1H), 7.86 (s, 1H), 7.78 (s, 1H), 4.11 (s, 3H).

1D. Preparation of 5-(4-Amino-2-methoxyphenyl) oxazole

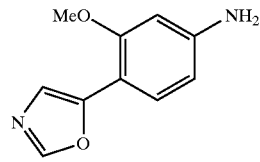

In a 2 L hydrogenation flask was placed 1C (130.0 g, 0.6131 mol), Pd/C (10%, 26.2 g) and absolute EtOH (1280 mL). The mixture was hydrogenated at 35-45 psi H$_2$ until the reaction was complete. The mixture was filtered over a pad of celite (20 g) and the cake was washed with EtOH (3×100 mL). The filtrate was concentrated to a volume of 350 mL. Heptane (500 mL) was added to the resulting slurry. After stirring for 2 hours at room temperature, the slurry was filtered. The cake was washed with heptane (3×100 mL) and air-dried to give 80.0 g of 5-(4-amino-2-methoxyphenyl) oxazole (1D). Another 30.2 g of product was recovered from the mother liquor affording a total yield of 95%. $^1$H NMR (CDCl$_3$) d 7.88 (s, 1H), 7.60 (d, J=8.4 Hz, 1H), 7.41 (s, 1H), 6.41 (dd, J=8.4, 2.1 Hz, 1H), 3.34 (d, J=2.1 Hz, 1H), 3.98 (bs, 2H), 3.94 (s, 3H).

1E. Preparation of N-(3-Cyanophenyl)-N'-[3-methoxy-4-(5-oxazolyl)phenyl]urea

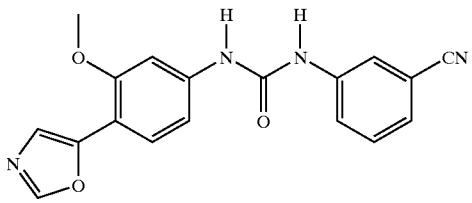

3-Methoxy-4-(5-oxazolyl)aniline, 1D (1.00 g, 5.26 mmol) and 3-cyanophenyl isocyanate (1.17 g, 7.89 mmol) in DCM (40 mL) were stirred at rt for 20 h. The precipitate formed was collected by filtration, followed by washing with dichlorometnane to provide 1E (1.57 g, 89% yield) as a yellow solid. (LC/MS retention time=3.67 min.; M+=335. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

1F. Preparation of the TFA salt of N-[3-(Aminomethyl)phenyl]-N'-[3-methoxy-4-(5-oxazolyl)phenyl]urea

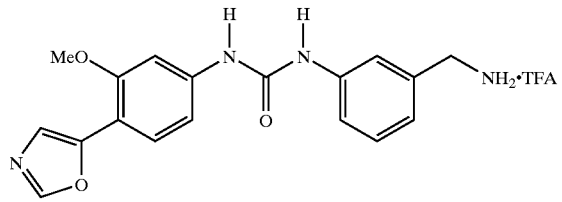

A suspension of 1E (421 mg, 1.26 mmol) and 10% Pd/C (80 mg) in 3:1 MeOH/TFA (100 mL) was stirred under a hydrogen environment provided by a balloon for 16 h. After the Pd/C and solvent were removed by filtration and evaporation, respectively, the residue was dissolved in water (50 mL) which resulted in a cloudy solution. To the solution was added MeOH until the cloudiness disappeared. The solution was washed with DCM (3×30 mL) and then concentrated to approximately 40 mL. The remaining solution was then lyophilized to provide 1F (477 mg, 84% yield) as a white powder. (LC/MS retention time=2.86 min.; M$^+$=339. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

Preparation of N-[3-[[[(Cyanoamino)phenoxymethylene]amino]methyl]phenyl]-N'-[3-methoxy-4-(5-oxazolyl)phenyl]urea

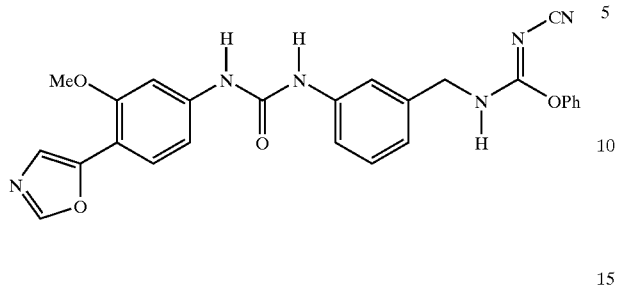

To a suspension of 1F (0.150 g, 0.220 mmol) in 50 ml of acetonitrile was added triethylamine (0.092 g, 0.660 mmol). The mixture was stirred until the solution became homogeneous. Diphenyl cyanocarbonimitate (0.109 g, 0.440 mmol) was added, and the reaction mixture was stirred at reflux for 14 h. The reaction was cooled, and the solvent was removed under reduced pressure to give a yellowish oil which was subjected to silica gel chromatography to give 0.079 g (75%) of 1 as a white solid. The product was determined to be 86% pure by HPLC (Retention time=3.94 min. Colunm: YMC S5 ODS 4.6×5.0 mm Ballistic. Solvent A=10% MeOH, 90% $H_2O$, 0.2% $H_3PO_4$; Solvent B=90% MeOH, 10% $H_2O$, 0.2% $H_3PO_4$).

EXAMPLE 2

Preparation N-[3-[[[Amino(cyanoamino)methylene]amino]methyl]phenyl]-N'-3-methoxy-4-(5-oxazolyl)phenyl]urea

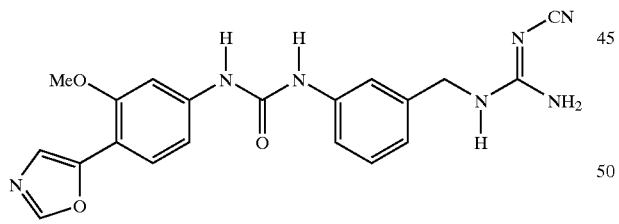

A solution of 1 (35 mg, 0.072 mmol) and ammonia (2.0 M EtOH solution, 4.0 mL, 8.0 mmol) in EtOH (4 mL) was heated in a sealed tube at 80° C. for 15 h. After the solvent was evaporated under reduced pressure, the residue was subjected to column chromatography (10% MeOH/$CHCl_3$) to afford compound 2 (19 mg, 66% yield) as a white solid. (LC/MS retention time=3.30 min.; $M^+$=406. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 3

Preparation of N-[3-[[[(Cyanoamino)(4-morpholinyl)methylene]amino]methyl]phenyl]-N'-[3-methoxy-4-(5-oxazolyl)phenyl]urea

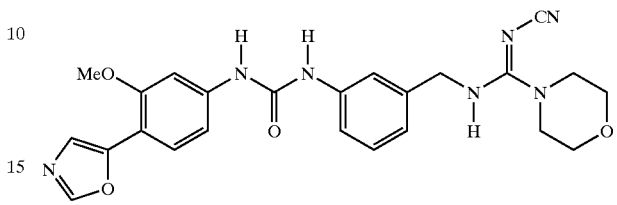

To 1 (0.029 g, 0.060 mmol) in 7 mL of acetonitrile was added excess morpholine (15.7 µL, 0.180 mmol). The mixture was heated at reflux for 48 h, cooled to rt, and the solvent was removed under reduced pressure. The residue was subjected to silica gel chromatography to give 14 mg of a residue which by HPLC contained 51% of 3. The residue was subjected to preparative HPLC to give 2.1 mg of 3 as a white solid which was 98% pure by LC/MS (retention time=3.32 min.; $M^+$=476.27. Column: YMC S5 ODS 4.6× 5.0 mm Ballistic. Solvent A=10% MeOH, 90% $H_2O$, 0.1% TFA; Solvent B=90% MeOH, 10% $H_2O$, 0.1% TFA).

EXAMPLE 4

Preparation of N-[3-[[[(Cyanoamino)[[2-(1H-imidazol-4-yl)ethyl]amino]methylene]-amino]methyl]phenyl]-N'-[3-methoxy-4-(5-oxazolyl)phenyl]urea

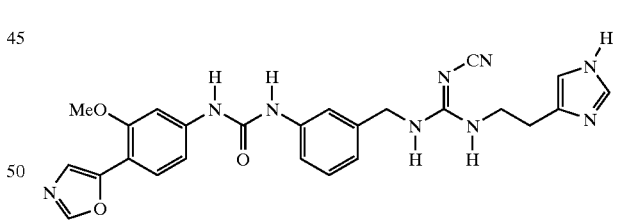

To Example 1 (0.012 g, 0.025 mmol) in 4 mL of acetonitrile was added histamine (3.0 mg, 0.025 mmol). The mixture was heated at reflux for 16 h, cooled to rt, and the solvent was removed under reduced pressure. The resulting residue was washed with ether and methylene chloride to give a white solid. The mixture was subjected to preparative HPLC to give 2.8 mg of Example 4 as a yellow solid which was 100% pure by HPLC (retention time=3.01 min.; $M^+$=500.30. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 5

Preparation of N-[3-[[[(Cyanoamino)(4-hydroxy-1-piperidinyl)methylene]amino]methyl]phenyl]-N'-[3-methoxy-4-(5-oxazolyl)phenyl]urea

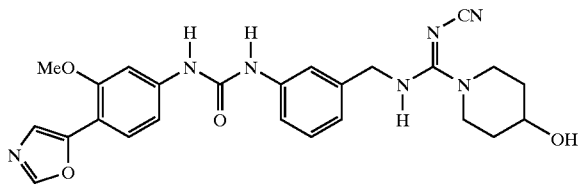

A mixture of 1 (0.010 g, 0.021 mmol) and 4-hydroxypiperidine in 3 mL of acetonitrile in a sealed tube was heated at approximately 1 00° C. for 48 h. After the reaction had cooled, the solvent was removed under reduced pressure. The resulting residue was washed with ether and DCM to give 10 mg of a yellow solid residue which was 71% pure by HPLC. The mixture was subjected to preparative HPLC to give 4.0 mg of 5 as a yellow oil, which was 96% pure by LC/MS (retention time=3.16) (M+H)$^+$490.3$^+$. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 6

Preparation of N-[3-[[[(Cyanoamino)(3-hydroxy-1-piperidinyl)methylene]amino]methyl]phenyl]-N'-[3-methoxy-4-(5-oxazolyl)phenyl]urea

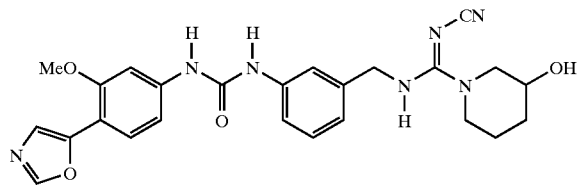

A mixture of 1 (0.010 g, 0.021 mmol) and 3-hydroxypiperidine in 3 mL of acetonitrile in a sealed tube was heated at approximately 100° C. for 48 h. After the reaction had cooled, the solvent was removed under reduced pressure. The resulting residue was washed with ether and DCM to give a yellow solid. The mixture was subjected to preparative HPLC to give 3.4 mg of 6 as a yellow solid which was 100% pure by LC/MS (retention time=3.17 min; (M+H)$^+$490.3$^+$. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 7

Preparation of N-[3-[[[(Cyanoamino)(cyclohexylamino)methylene]amino]methyl]phenyl]-N'-[3-methoxy-4-(5-oxazolyl)phenyl]urea

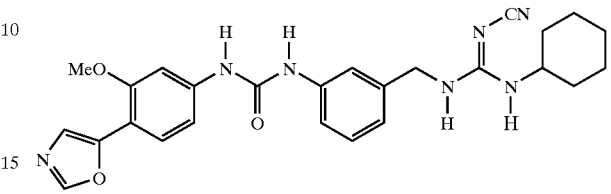

A mixture of 1 (0.015 g, 0.031 mmol) and cyclohexylamine (4.30 PL, 0.037 mmol) in 4 mL of acetonitrile in a sealed tube was heated at 110° C. for 48 h. After the reaction had cooled, the solvent was removed under reduced pressure. The resulting residue was washed with ether and DCM to give a residue which contained 72% of 7 by HPLC. The mixture was subjected to preparative HPLC to give 5.30 mg (35%) of the product as a pale yellow solid which was 100% pure by LC/MS (retention time=4.18 min.; M$^+$=488.25. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 8

Preparation of N-[3-[[[(Cyanoamino)[(4-pyridinylmethyl)amino]methylene]amino]methyl]phenyl]-N'-[3-methoxy-4-(5-oxazolyl)phenyl]urea

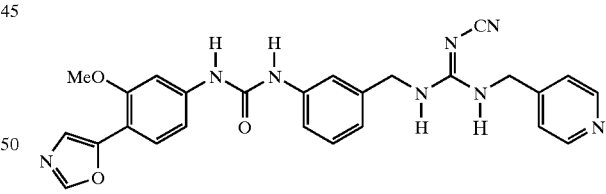

A mixture of 1 (0.015 g, 0.031 mmol) and 4-(aminomethyl)pyridine (3.80 μL, 0.037 mmol) in 4 mL of acetonitrile in a sealed tube was heated at 110° C. for 48 h. After the reaction had cooled, the solvent was removed under reduced pressure. The resulting residue was washed with ether and subjected to preparative HPLC to give 5.00 mg (33%) of 8 as an orange solid which was 100% pure by LC/MS (retention time=3.05 min.; M$^+$=497.26. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 9

Preparation of N-[3-[[[(Cyanoamino)[[(tetrahydro-2-furanyl)methyl]amino]methylene]-amino]methyl]phenyl]-N'-[3-methoxy-4-(5-oxazolyl)phenyl]urea

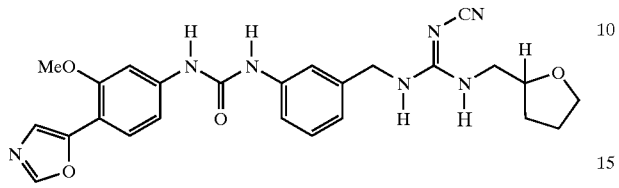

A mixture of 1 (0.015 g, 0.031 mmol) and tetrahydrofurfurylamine (3.90 μL, 0.037 mmol) in 4 mL of acetonitrile in a sealed tube was heated at 110° C. for 48 h. After the reaction had cooled, the solvent was removed under reduced pressure. The resulting residue was washed with ether, washed with DCM, and subjected to preparative HPLC to give 4.3 mg (29%) of 9 as a yellow solid which was 98% pure by LC/MS (retention time=3.65 min.; M+=490.23. Column: YMC S5 ODS 4.6×5.0 mm Ballistic. Solvent A=10% MeOH, 90% H$_2$O, 0.1% TFA; Solvent B =90% MeOH, 10% H$_2$O, 0.1% TFA).

EXAMPLE 10

Preparation of N-[3-[[[(Cyanoamino) [4-(2-hydroxyethyl)-1-piperazinyl]methylene]amino]methyl]phenyl]-N'-[3-methoxy-4-(5-oxazolyl)phenyl]urea

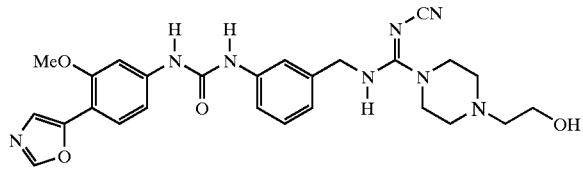

A mixture of 1 (0.031 g, 0.021 mmol) and 1-(2-hydroxyethyl)piperazine (4.60 μL, 0.037 mmol) in 4 mL of acetonitrile in a sealed tube was heated at 110° C. for 18 h. After the reaction had cooled, the solvent was removed under reduced pressure. The resulting residue was washed with ether and DCM to give a residue which contained 78% of 10 by HPLC. The mixture was subjected to preparative HPLC to give 3.80 mg (24%) of the product as a pale yellow solid which was 96% pure by LC/MS (retention time=3.10 min.; M+=519.30. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 11

Preparation of N-[3-[[[(Cyanoamino)(methylamino)methylene]amino]methyl]phenyl]-N'-[3-methoxy-4-(5-oxazolyl)phenyl]urea

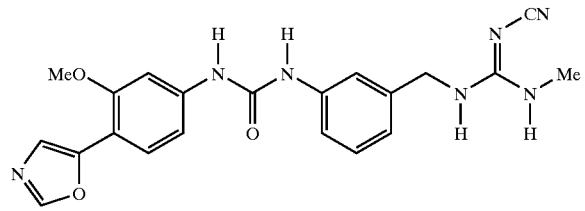

A mixture of 1 (0.020 g, 0.042 mmol) and methylamine (0.101 mL of a 2.0 M solution in THF, 0.21 mmol) in 4 mL of acetonitrile in a sealed tube was heated at 102° C. for 48 h. After the reaction had cooled, the solvent was removed under reduced pressure. The resulting residue was washed with ether, washed with DCM, and subjected to preparative HPLC to give 4.8 mg (28%) of 11 as a white solid which was 99% pure by LC/MS (retention time=3.42 min.; M+=420.19. Column: Shimadzu S5 C18 4.6×50 mm Ballistic. Solvent A=10% MeOH, 90% H$_2$O, 0.1% TFA; Solvent B=90% MeOH, 10% H$_2$O, 0.1% TFA).

EXAMPLE 12

Preparation of (S)-N-[3-[[[(Cyanoamino)[(tetrahydro-2-furanylmethyl)amino]-methylene]amino]methyl]phenyl]-N'-[3-methoxy-4-(5-oxazolyl)phenyl]urea

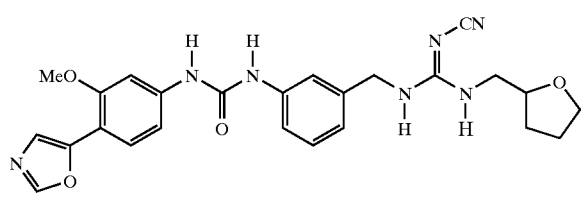

A mixture of 1 (0.020 g, 0.042 mmol) and (S)-(+)-tetrahydrofurfurylamine (5.1 μL, 0.050 mmol) in 4 mL of acetonitrile in a sealed tube was heated at 102° C. for 65 h. After the reaction had cooled, the solvent was removed under reduced pressure. The resulting residue was washed with ether, washed with DCM, and subjected to preparative HPLC to give 1.44 mg of 12 as a white solid which was 98% pure by LC/MS (retention time=3.69 min.; M+=490.26. Column: Shimadzu S5 C18 4.6×50 mm Ballistic. Solvent A=10% MeOH, 90% H$_2$O, 0.1% TFA; Solvent B=90% MeOH, 10% H$_2$O, 0.1% TFA).

EXAMPLE 13

Preparation of (R)-N-[3-[[[(Cyanoamino)[(tetrahydro-2-furanylmethyl)amino]-methylene]amino]methyl]phenyl]-N-[3-methoxy-4-(5-oxazolyl)phenyl]urea

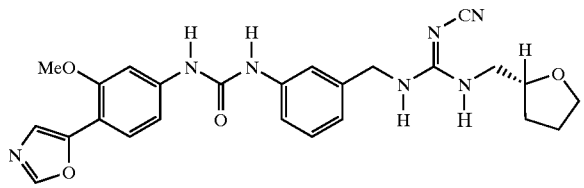

A mixture of 1 (0.020 g, 0.042 mmol) and (R)-(-)-tetrahydrofurfurylamine (5.1 μL, 0.050 mmol) in 4 mL of acetonitrile in a sealed tube was heated at 102° C. for 65 h. After the reaction had cooled, the solvent was removed under reduced pressure. The resulting residue was washed with ether, washed with DCM, and subjected to preparative HPLC to give 4.7 mg (24%) of 13 as a white solid which was 98% pure by LC/MS (retention time=3.69 min.; M+=490.26. Column: Shimadzu S5 C18 4.6×50 mm Ballistic. Solvent A=10% MeOH, 90% H$_2$O, 0.1% TFA; Solvent B=90% MeOH, 10% H$_2$O, 0.1% TFA).

EXAMPLE 14

Preparation of N-[3-[[[(Cyanoamino)[(tetrahydro-2-furanyl)methoxy]methylene]amino]-methyl]phenyl]-N'-[3-methoxy-4-(5-oxazolyl)phenyl]urea

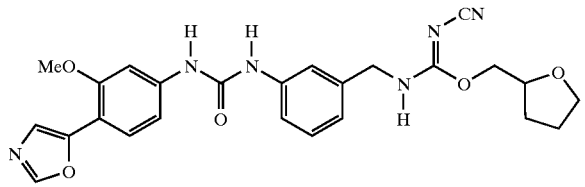

To a mixture of 1 (0.040 g, 0.042 mmol) and tetrahydrofurfuryl alcohol (16.1 μL, 0.166 mmol) in 7 mL of anhydrous THF at rt was added 60% NaH (13.0 mg, 0.332 mmol). The mixture was heated overnight at reflux, and then quenched with a small amount of water. The organic layer was carefully collected, and the aqueous residue was extracted several times with ethyl acetate. The organic layer was dried over anhydrous sodium sulfate and concentrated under reduced pressure. Preparative HPLC of the residue provided 12.1 mg (30%) of Example 14 as a white solid which was 99% pure by LC/MS (retention time=3.84 min.; M+=491.19. Column: Shimadzu S5 C18 4.6×50 mm Ballistic. Solvent A=10% MeOH, 90% H$_2$O, 0.1% TFA; Solvent B=90% MeOH, 10% H$_2$O, 0.1% TFA).

EXAMPLE 15

Preparation of N-[3-[[[(Cyanoamino)methoxymethyene]amino]methyl]phenyl]-N'-[3-methoxy-4-(5-oxazolyl)phenyl]urea

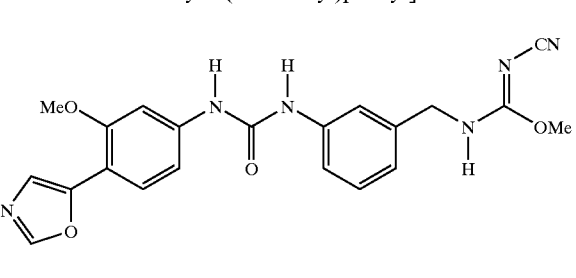

To a mixture of Example 1 (0.045 g, 0.093 mmol) and MeOH (30 μL, 0.746 mmol) in 5 mL of anhydrous THF at rt was added 60% NaH (14.0 mg, 0.373 mmol). The mixture was heated overnight at 50° C. and then quenched with a small amount of sat'd aq. ammonium chloride. The organic layer was removed under reduced pressure. The resulting solid was washed with ether several times and then diluted with MeOH. The sodium chloride salt was removed by filtration, and the filtrate was concentrated to give a tan solid which was washed several times with DCM to give 35.8 mg (92%) of Example 15 as an off-white solid. The product was 100% pure by analytical HPLC with a retention time of 3.66 min (Colunmn: YMC S5 ODS 4.6×50 mm Ballistic; Solvent A=10% MeOH, 90% H$_2$O, 0.2% H$_3$PO$_4$; Solvent B=90% MeOH, 10% H$_2$O, 0.2% H$_3$PO$_4$) and a LC/MS M$^{+1}$=421.21 (retention time=3.69 min.; Column: Shimadzu S5 C18 4.6× 50 mm Ballistic. Solvent A=10% MeOH, 90% H$_2$O, 0.1% TFA; Solvent B=90% MeOH, 10% H$_2$O, 0.1% TFA).

EXAMPLE 16

Preparation of N-[3-[[[(Cyanoamino)[(tetrahydro-3-furanyl)methoxy]methylene]amino]-methyl]phenyl]-N'-[3-methoxy-4-(5-oxazolyl)phenyl]urea

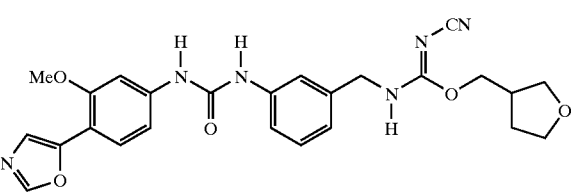

To a mixture of 1 (0.050 g, 0. 104 mmol) and tetrahydro-3-furanmethanol (80 μL, 0.829 mmol) in 6.5 mL of anhydrous THF at rt was added 60% NaH (16.6 mg, 0.415 mmol). The mixture was heated overnight at ~50° C. and then quenched with a small amount of sat'd aqueous ammonium chloride. The organic layer was removed under reduced pressure. The resulting solid was washed with ether several times and then diluted with MeOH. The sodium chloride salt was removed by filtration. Concentration followed by purification of the resulting residue by preparative HPLC afforded 2.9 mg of Example 16 as a white solid. The product was 100% pure by analytical HPLC with a retention time of 3.70 min (Column: YMC S5 ODS 4.6×50 mm Ballistic; Solvent A=10% MeOH, 90% H$_2$O, 0.2% H$_3$PO$_4$; Solvent B=90% MeOH, 10% H$_2$O, 0.2% H$_3$PO$_4$) and a LC/MS M$^{+1}$=491.24 (retention time=3.72 min.; Column: Shimadzu S5 C18 4.6×50 mm Ballistic. Solvent A=10% MeOH, 90% H$_2$O, 0.1% TFA; Solvent B=90% MeOH, 10% H$_2$O, 0.1% TFA).

EXAMPLE 17

Preparation of N-[3-[[Amino(cyanoamino)methylene]amino]phenyl]-N'-[3-methoxy-4-(5-oxazolyl)phenyl]urea

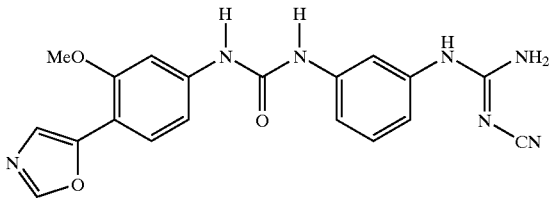

17A. Preparation of N-(3-nitrophenyl)-N'-[3-methoxy-4-(5-oxazolyl)phenyl]urea

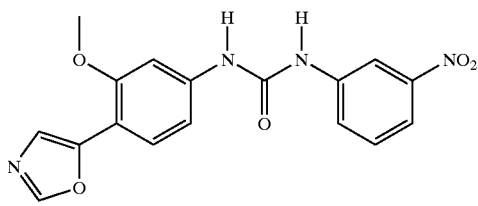

To a solution of 600 mg (3.2 mmol) of 1D in 20 ml of methylene chloride was added, as a solid, 525 mg (3.2 mmol) of m-nitrophenylisocyanate. A voluminous precipitate was obtained. Stirring was continued overnight. The precipitate was filtered and washed with methylene chloride to afford 1.1 g (3.1 mmol, 97%) of compound 17A as a yellow solid.

17B. Preparation of N-(3-aminophenyl)-N'-3-methoxy-4-(5-oxazolyl)phenyl]urea

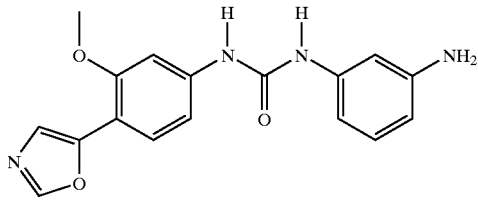

A solution of 0.7 g (2 mmol) of 17A in 60 ml of dioxane and 30 ml of MeOH was hydrogenated at rt and one atmosphere pressure over 0.14 g of 10% Pd/C catalyst. The catalyst was removed by filtration through Celite. The filtrate was evaporated to dryness to yield 0.3 g of 17B as a tan solid. The filter cake was suspended in dioxane—MeOH and stirred at 50° C. for 1 hr. The hot solution was again filtered, and the filtrate evaporated to dryness to yield an additional 0.6 g of material. The combined batches were triturated with methylene chloride and the insolubles filtered to give 645 mg (2 mmoles, 100%) of 17B as a light tan powder.

17C N-[3-[[rAmino(cyanoamino)methylene]amino]phenyl]-N-[3-methoxy-4-(5-oxazolyl)phenyl]urea To a solution of 50 mg (0.15 mmol) of 17B in 1 ml of DMF was added excess HCl—ether. A precipitate was obtained. Stirring was continued for 0.5 hr and the slurry was then evaporated to dryness. The residue was diluted with 2 nil of DMF and 40 mg (0.45 mmol) of sodium dicyanamide added. The reaction was heated at 50° C. for 3 hr during which time a lightly cloudy, pale yellow solution was obtained. After removal of the solvent, the residue was diluted with 3 ml of water and stirred for 1 hr. The insolubles were removed by filtration to give 76 mg of the crude product. This material was dissolved into MeOH and absorbed onto approx. 1 g of silica gel and subjected to flash chromatography on a 30 cc column of silica gel. Elution with 5% MeOH-EtOAc afforded 9 mg (0.023 mmol, 15%) of 17C as a pale yellow solid. (M+H)$^+$392$^+$.

Although the present invention has been described in some detail by way of illustration and example for purposes of clarity and understanding, it will be apparent that certain changes and modifications may be practiced within the scope of the appended claims.

We claim:
1. A compound having the formula,

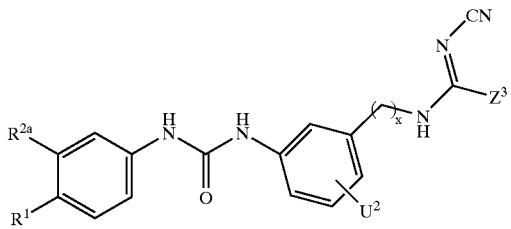

or a pharmaceutically acceptable salt thereof, in which
$U_2$ is selected from $R^{10}$ and $R^{11}$;
$Z^3$ is selected from $OR^2$ and $NR^3R^4$;
$R^1$ is oxazolyl optionally substituted with oxo (==O); and optionally having up to 3 substituents selected from $R^2$ and $R^3$;
$R^2$ is selected from halogen, CN, $NO_2$, $CF_3$, —($C_0$–$C_4$ alkyl)$OR^3$, $OCF_3$, $OC(O)R^3$, $OC(O)OR^3$, $OC(O)NR^3R^4$, —($C_0$–$C_4$ alkyl)$C(O)R^3$, —($C_0$–$C_4$alkyl)$C(O)OR^3$, —($C_0$–$C_4$alkyl)$C(O)NR^3R^4$, —($C_0$–$C_4$alkyl)$SR^3$, —($C_0$–$C_4$ alkyl)$S(O)R^5$, —($C_0$–$C_4$alkyl)$S(O)_2R^5$, —($C_0$–$C_4$ alkyl)$S(O)_2NR^3R^4$, —($C_0$–$C_4$alkyl)$NR^3R^4$, —($C_0$–$C_4$ alkyl)$NR^3C(O)NR^4$, —($C_0$–$C_4$ alkyl)$NR^3C(O)R_4$, —($C_0$–$C_4$ alkyl)$NR^3C(O)OR^5$, and —($C_0$–$C_4$ alkyl)$NR^3S(O)_2R^5$;
$R^{2a}$ is selected from hydrogen, halogen, CN, $NO_2$, $CF_3$, —($C_0$–$C_4$ alkyl)$OR^3$, $OCF_3$, $OC(O)R^3$, $OC(O)OR^3$, $OC(O)NR^3R^4$, —($C_0$-$C_4$ alkyl)$C(O)R^3$, —($C_0$–$C_4$alkyl)$C(O)OR^3$, —($C_0$–$C_4$alkyl)$C(O)NR^3R^4$, —($C_0$–$C_4$ alkyl)$SR^3$, —($C_0$–$C_4$ alkyl)$S(O)R^5$, —($C_0$–$C_4$alkyl)$S(O)_2R^5$, —($C_0$–$C_4$alkyl)$S(O)_2NR^3R^4$, —($C_0$–$C_4$alkyl)$NR^3R^4$, —($C_0$–$C_4$ alkyl)$NR^3C(O)NR^4$, —($C_0$–$C_4$ alkyl)$NR^3C(O)R^4$, —($C_0$–$C_4$ alkyl)$NR^3C(O)OR^5$, and —($C_0$–$C_4$ alkyl)$NR^3S(O)_2R^5$;
$R^3$ is selected from hydrogen, ($C_1$–$C_4$)alkyl, ($C_2$–$C_4$)alkenyl, aryl($C_0$–$C_4$)alkyl, heterocycle($C_0$–$C_4$)alkyl, and cycloalkyl($C_0$–$C_4$)alkyl, wherein said groups are substituted with 0–2 substituents independently selected from $R^6$;
$R^4$ is selected from hydrogen, ($C_1$–$C_4$)alkyl, ($C_2$–$C_4$)alkenyl, aryl($C_0$–$C_4$)alkyl, heterocycle($C_0$–$C_4$)alkyl, and cycloalkyl($C_0$–$C_4$)alkyl, wherein said groups are substituted with 0–2 substituents independently selected from $R^6$;
alternatively, $R^3$ and $R^4$, when both substituents are on the same nitrogen atom, as in (—$NR^3R^4$), can be taken together with the nitrogen atom to which they are attached to form a heterocycle selected from the group consisting of 1-piperidinyl, 1-morpholinyl, 1-pyrrolidinyl, and 1-piperazinyl, said heterocycle being optionally substituted with 0–3 groups selected from the group consisting of oxo, $R^6$, $(C_1-C_6)$alkyl, $C_3-C_7$ cycloalkyl$(C_0-C_4$alkyl$)$, $(C_1-C_6)$alkylcarbonyl, $C_3-C_7$cycloalkyl$(C_0-C_5$alkyl$)$carbonyl, $C_1-C_6$alkoxycarbonyl, $C_3-C_7$cycloalkyl$(C_0-C_5$ alkoxy)carbonyl, aryl$(C_0-C_5$alkyl), heterocycle$(C_0-C_5$ alkyl), aryl$(C_1-C_5$ alkoxy)carbonyl, heterocycle $(C_1-C_5$ alkoxy)carbonyl, $(C_1-C_6)$alkylsulfonyl, arylsulfonyl, and heterocyclesulfonyl;

$R^5$ is selected from $(C_1-C_4)$alkyl, $(C_2-C_4)$alkenyl, $(C_2-C_4)$alkynyl, aryl$(C_0-C_4)$ alkyl, heterocycle $(C_0-C_4)$alkyl, and cycloalkyl$(C_0-C_4)$alkyl, and each $R^5$ optionally comprises up to 2 substituents independently selected from $R^6$;

$R^6$ is selected from hydrogen, halogen, $NO_2$, CN, $C_1-C_4$alkyl, $C_3-C_{10}$ cycloalkyl, $C_2-C_6$alkenyl, haloalkyl, haloalkoxy, OH, hydroxy$C_1-C_4$alkyl, $C_1-C_4$ alkoxy, $(C_1-C_4$alkyl$)$carbonyl, $NH_2$, $(C_1-C_4$alkyl$)_{1-2}$alkylamino, $C_0-C_4$alkylthio, and $(C_1-C_4$alkyl$)$sulfonyl;

$R^{10}$ is selected from hydrogen, $(C_1-C_4)$alkyl, $(C_2-C_4)$alkenyl, $(C_2-C_4)$alkynyl, aryl, heterocycle, and cycloalkyl, and each $R^{10}$ optionally comprises up to 3 substituents selected from $R^{11}$ and $R^{12}$;

$R^{11}$ is selected from hydrogen, halogen, $NO_2$, CN, $(C_1-C_4)$alkyl, $C_3-C_{10}$ cycloalkyl, $(C_2-C_6)$alkenyl, $(C_2-C_6)$alkynyl, haloalkyl, haloalkoxy, OH, $C_1-C_4$alkoxy, $C_1-C_4$alkylcarbonyl, $NH_2$, $(C_1-C_4$alkyl$)_{1-2}$alkylamino—, $C_0-C_4$alkylthio-, and $C_1-C_4$ alkylsulfonyl;

$R^{12}$ is selected from hydrogen, alkyl, $(C_1-C_6)$alkoxy, $C_3-C_6$cycloalkyl, heterocycle and aryl; and x is 0, 1 or 2.

2. A compound according to claim 1, or a pharmaceutically-acceptable salt thereof, wherein $R^{2a}$ is $OR^3$ and said $R^3$ is selected from hydrogen, $(C_1-C_4)$alkyl, and $(C_2-C_4)$alkenyl.

3. A compound according to claim 1, or a pharmaceutically-acceptable salt thereof, wherein $Z^3$ is selected from $O(C_{1-4}$alkyl, $O($phenyl$)$, $O(CH_2)_{0-2}$heterocycle, $O(CH_2)_{0-2}$cycloalkyl, $NH_2$, $NH(C_{1-4}$alkyl, $N(C_{1-4}$alkyl$)_2$, $NH(CH_2)_{0-2}$heterocycle, $NH(CH_2)_{0-2}$cycloalkyl, $—(CH_2)_{0-2}$heterocycle, $(CH_2)_{0-2}$cycloalkyl, morpholinyl, piperidinyl, and piperazinyl, wherein said $Z^3$ groups are substituted with 0–2 substituents independently selected from $R^6$; and $R^6$ is selected from hydrogen, halogen, $NO_2$, CN, $C_1-C_4$alkyl, $C_3-C_{10}$ cycloalkyl, $C_2-C_6$alkenyl, haloalkyl, haloalkoxy, OH, hydroxy $C_1-C_4$alkyl, $C_1-C_4$ alkoxy, $(C_1-C_4$alkyl$)$carbonyl, $NH_2$, $(C_1-C_4$ alkyl$)_{1-2}$alkylamino, $C_0-C_4$alkylthio, and $(C_1-C_4$alkyl$)$sulfonyl.

4. A compound selected from the group consisting of (i):
N-[3-[[[(Cyanoamino)phenoxymethylene]amino]methyl] phenyl]-N'-[3-methoxy-4-(5-oxazolyl)phenyl]urea;
N-[3-[[[Amino(cyanoamino)methylene]amino]methyl] phenyl]-N'-[3-methoxy-4-(5-oxazolyl)phenyl]urea;
N-[3-[[[(Cyanoamino)(4-morpholinyl)methylene]amino] methyl]phenyl]-N'-[3-methoxy-4-(5-oxazolyl)phenyl] urea;
N-[3-[[[(Cyanoamino)[[2-(1H-imidazol-4-yl)ethyl]amino] methylene]-amino]methyl]phenyl]-N'-[3-methoxy-4-(5-oxazolyl)phenyl]urea;
N-[3-[[[(Cyanoamino)(4-hydroxy-1-piperidinyl)methylene] amino]-methyl]phenyl]-N'-[3-methoxy-4-(5-oxazolyl) phenyl]urea;
N-[3-[[[(Cyanoamino)(3-hydroxy-1-piperidinyl)methylene] amino]-methyl]phenyl]-N'-[3-methoxy-4-(5-oxazolyl) phenyl]urea;
N-[3-[[[(Cyanoamino)(cyclohexylamino)methylene]amino] methyl]-phenyl]-N'-[3-methoxy-4-(5-oxazolyl)phenyl] urea;
N-[3-[[[(Cyanoamino)[(4-pyridinylmethyl)amino] methylene]amino]-methyl]phenyl]-N'-[3-methoxy-4-(5-oxazolyl)phenyl]urea;
N-[3-[[[(Cyanoamino)[[(tetrahydro-2-furanyl)methyl] amino]methylene]-amino]methyl]phenyl]-N'-[3-methoxy-4-(5-oxazolyl)phenyl]urea;
N-[3-[[[(Cyanoamino)[4-(2-hydroxyethyl)-1-piperazinyl] methylene]-amino]methyl]phenyl]-N'-[3-methoxy-4-(5-oxazolyl)phenyl]urea;
N-[3-[[[(Cyanoamino)(methylamino)methylene]amino] methyl]phenyl]-N'-[3-methoxy-4-(5-oxazolyl)phenyl] urea;
(R)-N-[3-[[[(Cyanoamino)[(tetrahydro-2-furanylmethyl) amino]-methylene]amino]methyl]phenyl]-N'-[3-methoxy-4-(5-oxazolyl)phenyl]urea;
(S)-N-[3-[[[(Cyanoamino)[(tetrahydro-2-furanylmethyl) amino]-methylene]amino]methyl]phenyl]-N'-[3-methoxy-4-(5-oxazolyl)phenyl]urea;
N-[3-[[[(Cyanoamino)[(tetrahydro-2-furanyl)methoxy] methylene]amino]-methyl]phenyl]-N'[3-methoxy-4-(5-oxazolyl)phenyl]urea;
N-[3-[[[(Cyanoamino)methoxymethylene]amino]methyl] phenyl]-N'-[3-methoxy-4-(5-oxazolyl)phenyl]urea;
N-[3-[[[(Cyanoamino)[(tetrahydro-3-furanyl)methoxy] methylene]amino]-methyl]phenyl]-N'-[3-methoxy-4-(5-oxazolyl)phenyl]urea; and
N-[3-[[Amino(cyanoamino)methylene]amino]phenyl]-N'-[3-methoxy-4-(5-oxazolyl)phenyl]urea; and (ii) a pharmaceutically-acceptable salt, prodrug, or solvate thereof.

5. A pharmaceutical composition comprising at least one compound of claim 1, or a pharmaceutically acceptable salt thereof, and a pharmaceutically acceptable carrier, adjuvent or vehicle.

6. A compound according to claim 1, or a pharmaceutically acceptable salt thereof, in which:

$U^2$ is selected from hydrogen and $(C_1-C_4)$alkyl;

$R^1$ is oxazolyl optionally having up to 1 substituent selected from $R^2$;

$R^2$ is selected from halogen, CN, $CF_3$, $—(C_0-C_4$ alkyl$)$OH, $—(C_0-C_4$ alkyl$)$O(alkyl), $OCF_3$, $—(C_0-C_4$ alkyl$)$C(O)H, $—(C_0-C_4$alkyl$)$C(O)OH, $—(C_0-C_4$ alkyl$)$SH, $—(C_0-C_4$ alkyl$)$C(O)(alkyl), $—(C_0-C_4$alkyl$)$C(O)O (alkyl), $—(C_0-C_4$ alkyl$)$S(alkyl), $—(C_0-C_4$ alkyl$)$S(O) (alkyl), $—(C_0-C_4$alkyl$)$S(O)2(alkyl), $—(C_0-C_4$ alkyl$)$ $NH_2$, $—(C_0-C_4$ alkyl$)$NH$(C_{1-4})$alkyl, and $—(C_0-C_4$ alkyl$)$N $(C_{1-4}$alkyl$)_2$;

$R^{2a}$ is selected from hydrogen, halogen, OH, $O(C_1-C_4)$ alkyl, and $O(C_2-C_4)$alkenyl; and x is 0 or 1.

7. A compound according to claim 6, or a pharmaceutically-acceptable salt thereof, in which:

$Z^3$ is selected from $O(C_{1-4})$alkyl, $O($phenyl$)$, $O(CH_2)_{0-2}$tetrahydrofuryl, $O(CH_2)_{0-2}$cycloalkyl, $(CH_2)_{0-2}$piperidinyl, $(CH_2)_{0-2}$piperazinyl, $(CH_2)_{0-2}$morpholinyl, $(CH_2)_{0-2}$pyridyl, $(CH_2)_{0-2}$imidazolyl, $(CH_2)_{0-2}(C_{3-7})$cycloalkyl, $NH_2$, NH($C_{1-4}$)alkyl, N($C_{1-4}$alkyl)$_2$, NH(CH$_2$)$_{0-2}$cycloalkyl, NH(CH$_2$)$_{0-2}$tetrahydrofuryl, NH(CH$_2$)$_{0-2}$piperidinyl, NH(CH$_2$)$_{0-2}$piperazinyl, NH(CH$_2$)$_{0-2}$morpholinyl, NH(CH$_2$)$_{0-2}$pyridyl, and NH(CH$_2$)$_{0-2}$imidazolyl, wherein said $Z^3$ groups are substituted with 0–2 substituents independently selected from $R^6$; and $R^6$ is selected from hydrogen, halogen, NO$_2$, CN, $C_1$–$C_4$alkyl, $C_3$–$C_{10}$ cycloalkyl, $C_2$–$C_6$alkenyl, haloalkyl, haloalkoxy, OH, hydroxy$C_1$–$C_4$alkyl, $C_1$–$C_4$ alkoxy, ($C_1$–$C_4$alkyl)carbonyl, NH$_2$, NH$_2$, NH($C_{1-4}$) alkyl, N($C_{1-4}$alkyl)$_2$, SH, S($C_1$–$C_4$alkyl), and ($C_1$–$C_4$alkyl)sulfonyl.

8. A compound according to claim 1 having the formula,

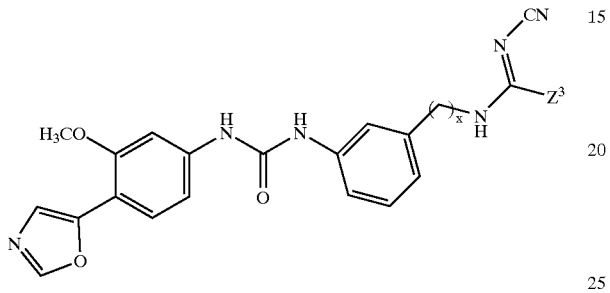

or a pharmaceutically acceptable salt thereof.

9. A compound according to claim 8, or a pharmaceutically-acceptable salt thereof, in which:

$Z^3$ is selected from O($C_{1-4}$)alkyl, O(phenyl), O(CH$_2$)$_{0-2}$tetrahydrofuryl, O(CH$_2$)$_{0-2}$cycloalkyl, (CH$_2$)$_{0-2}$piperidinyl, (CH$_2$)$_{0-2}$piperazinyl, (CH$_2$)$_{0-2}$morpholinyl, (CH$_2$)$_{0-2}$pyridyl, (CH$_2$)$_{0-2}$imidazolyl, (CH$_2$)$_{0-2}$($C_{3-7}$)cycloalkyl, NH$_2$, NH($C_{1-4}$alkyl), N($C_{1-4}$alkyl)$_2$, NH(CH$_2$)$_{0-2}$cycloalkyl, NH(CH$_2$)$_{0-2}$tetrahydrofuryl, and NH(CH$_2$)$_{0-2}$pyridyl, wherein said $Z^3$ groups are substituted with 0–2 substituents independently selected from $R^6$;

$R^6$ is selected from halogen, CN, $C_1$–$C_4$alkyl, haloalkyl, haloalkoxy, OH, hydroxy$C_1$–$C_4$alkyl, $C_1$–$C_4$ alkoxy, NH$_2$, NH$_2$, NH($C_{1-4}$)alkyl, and N($C_{1-4}$alkyl)$_2$; and x is 0 or 1.

10. A method for the treatment of a disease selected from inflammatory bowel disease, hepatitis B, hepatitis C, herpes simplex I, herpes simplex II, rheumatoid arthritis, asthma, and transplant rejection, said method comprising the step of administering to a subject in need thereof an effective amount of at least one compound of claim 1 or a pharmaceutically acceptable salt thereof.

* * * * *